(12) United States Patent
Oldfield et al.

(10) Patent No.: US 11,491,291 B2
(45) Date of Patent: Nov. 8, 2022

(54) METHODS AND APPARATUS FOR OXYGENATION AND/OR CO2 REMOVAL

(71) Applicant: Fisher & Paykel Healthcare Limited, Auckland (NZ)

(72) Inventors: Samantha Dale Oldfield, Auckland (NZ); Milanjot Singh Assi, Sydney (AU); Geraldine Keogh, Auckland (NZ); Callum James Thomas Spence, Auckland (NZ); Michael Robert Barraclough, Auckland (NZ); Matthew Jon Payton, Auckland (NZ); Laith Adeeb Hermez, Auckland (NZ); Thomas Heinrich Barnes, Surrey (GB); Craig Karl White, Auckland (NZ); Alicia Jerram Hunter Evans, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 484 days.

(21) Appl. No.: 15/562,848

(22) PCT Filed: Mar. 31, 2016

(86) PCT No.: PCT/IB2016/051820
§ 371 (c)(1),
(2) Date: Sep. 28, 2017

(87) PCT Pub. No.: WO2016/157106
PCT Pub. Date: Oct. 6, 2016

(65) Prior Publication Data
US 2018/0104426 A1  Apr. 19, 2018

Related U.S. Application Data

(60) Provisional application No. 62/140,794, filed on Mar. 31, 2015.

(51) Int. Cl.
*A61M 16/00* (2006.01)
*A61B 5/087* (2006.01)
(Continued)

(52) U.S. Cl.
CPC ....... *A61M 16/0069* (2014.02); *A61B 5/0205* (2013.01); *A61B 5/087* (2013.01);
(Continued)

(58) Field of Classification Search
None
See application file for complete search history.

(56) References Cited

U.S. PATENT DOCUMENTS

| | | |
|---|---|---|
| 3,410,264 A | 11/1968 | Frederik |
| 4,155,356 A | 5/1979 | Venegas |

(Continued)

FOREIGN PATENT DOCUMENTS

| | | |
|---|---|---|
| CN | 101448539 | 12/2012 |
| EP | 0127923 A2 | 12/1984 |

(Continued)

OTHER PUBLICATIONS

Caring for a Premature Baby (Accessed on Nov. 23, 2019)(Priority Date—Oct. 27, 2014) (Year: 2014).*

(Continued)

*Primary Examiner* — Valerie L Woodward
*Assistant Examiner* — Paige Kathleen Bugg
(74) *Attorney, Agent, or Firm* — Knobbe, Martens, Olson & Bear, LLP

(57) ABSTRACT

Described is an apparatus for oxygenation and/or CO2 clearance of a patient, comprising: a flow source or a connection for a flow source for providing a gas flow, a gas flow modulator, a controller to control the gas flow, wherein the controller is operable to: receive input relating to heart activity and/or trachea gas flow of the patient, and control (Continued)

the gas flow modulator to provide a varying gas flow with one or more oscillating components with a frequency or frequencies based on the heart activity and/or trachea flow of the patient.

28 Claims, 21 Drawing Sheets

(51) Int. Cl.
    *A61B 5/091*     (2006.01)
    *A61B 5/0205*     (2006.01)
    *A61B 5/145*     (2006.01)
    *A61M 16/06*     (2006.01)
    *A61M 16/12*     (2006.01)
    *A61M 16/16*     (2006.01)
    *A61M 16/20*     (2006.01)
    *A61M 16/10*     (2006.01)
    *A61B 5/024*     (2006.01)

(52) U.S. Cl.
    CPC .......... *A61B 5/091* (2013.01); *A61B 5/14542* (2013.01); *A61M 16/0006* (2014.02); *A61M 16/0096* (2013.01); *A61M 16/024* (2017.08); *A61M 16/0666* (2013.01); *A61M 16/12* (2013.01); *A61M 16/16* (2013.01); *A61M 16/202* (2014.02); *A61M 16/203* (2014.02); *A61M 16/209* (2014.02); *A61B 5/024* (2013.01); *A61M 16/107* (2014.02); *A61M 16/109* (2014.02); *A61M 16/161* (2014.02); *A61M 2016/0027* (2013.01); *A61M 2016/0033* (2013.01); *A61M 2016/1025* (2013.01); *A61M 2202/0208* (2013.01); *A61M 2202/0225* (2013.01); *A61M 2205/3303* (2013.01); *A61M 2205/3334* (2013.01); *A61M 2205/3368* (2013.01); *A61M 2205/502* (2013.01); *A61M 2205/52* (2013.01); *A61M 2230/04* (2013.01); *A61M 2230/06* (2013.01); *A61M 2230/10* (2013.01); *A61M 2230/202* (2013.01); *A61M 2230/205* (2013.01); *A61M 2230/42* (2013.01); *A61M 2230/432* (2013.01); *A61M 2230/60* (2013.01); *A61M 2230/63* (2013.01)

(56) References Cited

U.S. PATENT DOCUMENTS

| | | | |
|---|---|---|---|
| 4,719,910 A | 1/1988 | Jensen | |
| 4,805,612 A * | 2/1989 | Jensen | A61M 16/0486 128/204.21 |
| 4,821,709 A | 4/1989 | Jensen | |
| 5,165,398 A | 11/1992 | Bird | |
| 6,029,664 A | 2/2000 | Zdrojkowski et al. | |
| 6,029,665 A | 2/2000 | Berthon-Jones | |
| 6,085,747 A | 7/2000 | Axe et al. | |
| 6,193,677 B1 | 2/2001 | Cady | |
| 6,390,092 B1 | 5/2002 | Leehoven | |
| 6,446,629 B1 | 9/2002 | Takaki et al. | |
| 6,557,554 B1 | 5/2003 | Sugiura | |
| 6,934,579 B2 * | 8/2005 | Mantzaridis | A61B 5/1106 600/544 |
| 7,861,716 B2 | 1/2011 | Borrello | |
| 8,631,799 B2 | 1/2014 | Davenport et al. | |
| 2001/0009152 A1 * | 7/2001 | Bennarsten | A61M 16/085 128/204.21 |
| 2004/0069304 A1 | 4/2004 | Jam | |
| 2005/0121033 A1 | 6/2005 | Starr et al. | |
| 2005/0178383 A1 | 8/2005 | Mackie | |
| 2005/0257788 A1 | 11/2005 | Aylsworth et al. | |
| 2006/0005842 A1 | 1/2006 | Rashad et al. | |
| 2006/0042638 A1 * | 3/2006 | Niklewski | A61M 16/0051 128/207.18 |
| 2006/0162727 A1 | 7/2006 | Biondi et al. | |
| 2006/0174885 A1 | 8/2006 | Aylsworth et al. | |
| 2006/0174889 A1 * | 8/2006 | Noble | A61M 16/0666 128/206.11 |
| 2007/0113847 A1 | 5/2007 | Acker et al. | |
| 2007/0175473 A1 * | 8/2007 | Lewis | A61M 16/085 128/204.18 |
| 2007/0215154 A1 | 9/2007 | Borrello | |
| 2008/0142019 A1 | 6/2008 | Lewis et al. | |
| 2009/0007913 A1 | 1/2009 | Lee | |
| 2009/0126731 A1 | 5/2009 | Dunsmore | |
| 2009/0145428 A1 | 6/2009 | Sward et al. | |
| 2009/0156952 A1 | 6/2009 | Hunter et al. | |
| 2009/0253995 A1 | 10/2009 | Lewis et al. | |
| 2010/0078024 A1 | 4/2010 | Andreiux et al. | |
| 2010/0101583 A1 * | 4/2010 | Chen | A61B 5/4818 128/207.14 |
| 2010/0252037 A1 | 10/2010 | Wondka | |
| 2010/0319691 A1 | 12/2010 | Lurie et al. | |
| 2011/0114098 A1 | 5/2011 | Mcauley et al. | |
| 2011/0125052 A1 | 5/2011 | Davenport et al. | |
| 2011/0214676 A1 | 9/2011 | Allum | |
| 2012/0017904 A1 * | 1/2012 | Ratto | A61M 16/024 128/203.26 |
| 2012/0060840 A1 | 3/2012 | Refsland et al. | |
| 2012/0103337 A1 | 5/2012 | Avni | |
| 2012/0266882 A1 | 10/2012 | Dellaca et al. | |
| 2013/0012828 A1 | 1/2013 | Aylsworth | |
| 2013/0133655 A1 | 5/2013 | Kimm et al. | |
| 2014/0190481 A1 | 7/2014 | Jam | |
| 2014/0283834 A1 | 9/2014 | Shamir et al. | |
| 2014/0350429 A1 | 11/2014 | Truschel et al. | |
| 2015/0059751 A1 | 3/2015 | Cortez, Jr. et al. | |
| 2015/0119742 A1 * | 4/2015 | Tse | A61M 16/085 128/200.26 |
| 2015/0119743 A1 | 4/2015 | Maksym | |
| 2015/0182713 A1 | 7/2015 | Phuah et al. | |
| 2015/0258291 A1 * | 9/2015 | Richards-Kortum | A61M 16/0672 128/201.22 |
| 2015/0335851 A1 | 11/2015 | Cullen et al. | |
| 2015/0359982 A1 * | 12/2015 | Garde | A61M 16/024 128/202.22 |
| 2016/0193438 A1 * | 7/2016 | White | A61M 16/0051 128/203.12 |
| 2016/0228661 A1 | 8/2016 | Larsson | |
| 2016/0339191 A1 | 11/2016 | Kaczka | |
| 2016/0367779 A1 | 12/2016 | Landis et al. | |
| 2017/0087316 A1 | 3/2017 | White et al. | |
| 2017/0303821 A1 | 10/2017 | Hete | |
| 2018/0126110 A1 * | 5/2018 | Payton | A61M 16/104 |
| 2021/0052844 A1 | 2/2021 | Oldfield et al. | |

FOREIGN PATENT DOCUMENTS

| | | | |
|---|---|---|---|
| EP | 3259001 | 10/2018 | |
| GB | 2357037 | 6/2001 | |
| GB | 2442875 A | 4/2008 | |
| JP | 2001-500039 | 10/2004 | |
| JP | 2015-506802 | 3/2015 | |
| WO | WO 98/10818 A1 | 3/1998 | |
| WO | WO 03/066145 | 8/2003 | |
| WO | WO 2005/006941 | 1/2005 | |
| WO | WO 2005/011556 | 2/2005 | |
| WO | WO 2006/088007 | 8/2006 | |
| WO | WO 2008/030261 | 3/2008 | |
| WO | WO 2008/039703 | 4/2008 | |
| WO | WO 2009/094532 | 7/2009 | |
| WO | WO 2010/076704 | 7/2010 | |
| WO | WO 2011/007346 | 1/2011 | |
| WO | WO 2013/042007 | 3/2013 | |
| WO | WO-2013137753 A1 * | 9/2013 | ........ A61M 16/0875 |
| WO | WO 2013/148754 | 10/2013 | |
| WO | WO 2013/148901 | 10/2013 | |
| WO | WO 2013/172722 A1 | 11/2013 | |
| WO | WO-2013172722 A1 * | 11/2013 | ........ A61M 16/0666 |

(56) References Cited

FOREIGN PATENT DOCUMENTS

| WO | WO 2013/179181 A1 | 12/2013 |
|---|---|---|
| WO | WO 2014/111828 | 7/2014 |
| WO | WO 2014/140278 | 9/2014 |
| WO | WO 2014/196875 | 12/2014 |
| WO | WO 2015/033288 | 3/2015 |
| WO | WO 2015/174864 | 11/2015 |
| WO | WO 2016/063172 | 4/2016 |
| WO | WO 2016/079703 | 5/2016 |
| WO | WO 2016/157106 | 10/2016 |
| WO | WO 2017/187390 | 11/2017 |

OTHER PUBLICATIONS

European Examination Report dated Jun. 7, 2018 for European Application No. EP 14 841 727.2-1122.
European Examination Report dated Jun. 12, 2019 for European Application No. EP 16 771 502.8-1122.
International Searching Authority, Written Opinion of the International Searching Authority in re Int'l Appl. No. PCT/IB2016/051820, dated Jun. 30, 2016.
International Searching Authority, International Search Report in re Int'l Appl. No. PCT/IB/206/051820, dated Jun. 30, 2016.
Examination report for Chinese Application No. 201680027864.X dated Nov. 18, 2019, 8 pages.
Great Britain Examination Report for Application No. 1715384.2 dated Mar. 26, 2020, Part 1, 2 pages.
Great Britain Examination Report for Application No. 1715384.2 dated Mar. 26, 2020, Part 2, 2 pages.
Australian Examination Report for Application No. 2014316671, dated Dec. 10, 2018, 4 pages.
De Luca et al., Effect of Amplitude and Inspiratory Time in a Bench Model; Pediatric Pulmonology (2012); Copyright 2012 Wiley Periodicals, Inc.; 7 pages.
De Luca et al., Noninvasive high frequency oscillatory ventilation; Intensive Care Med (2010); Published Sep. 21, 2010; 7 pages.
DeBlasi et al., Noninvasive Respiratory Support Juvenile Rabbits, vol. 67, No. 6, 2010, Pediatric Research; 6 pages.
DiBlasi et al., Effective gas exchange paralysed juvenile rabbits, Apr. 7, 2010; Pediatric Research; 26 pages.
EPO Examination report; dated Jun. 7, 2018; 7 pages.
Examination Report for Japanese Patent Application 2017-551616 dated Mar. 3, 2020.
Extended European Search Report, Eurpean Application No. EP 14 84 1727, Mar. 7, 201, 7 pages.
International Search Report; PCT/IB2014/064245; dated Feb. 2, 2015; 11 pages.
Summary of objections for European Application No. 14841727.2 dated Dec. 12, 2019 in 6 pages.
Summons to attend oral proceedings for European Application No. 14841727.2 dated Dec. 12, 2019 in 2 pages.
Written Opinion; PCT/IB2014/064245; dated Feb. 2, 2015; 11 pages.
Australian Examination Report for Application No. 2016241573 dated Apr. 14, 2020, 5 pages.
Australian Examination Report for Australian Application No. 2019275640 dated Jun. 18, 2020; 5 pages.
Brighenti, C. et al., 'Effects of the Ventilator Patient Circuit on the Respiratory Parameter estimates: A Simulation Study', IFMBE Proceedings MEDICON, Modelling and Simulation of Physiological Systems, Jun. 12-15, 2001, Part II, pp. 915-918.
Georgia State University, Ohm's Law-Poiseuille's Law, Hyperphysics, http://hyperphysics.phy-astr-gsu-edu/hbase/electric/watcir2.html, Dec. 6, 2007.
Lim, M. W. et al., 'Relationship of inspiratory and expiratory times to upper airway resistance during pulsatile needle cricothyrotomy ventilation with generic delivery circuit', British Journal of Anaesthesia, 2010, V104(1), pp. 98-107.
Meraz, E. et al., 'Modeling Human Respiratory Impedance in Hispanic Asthmatic Children', Proceedings of the 29th Annual International Conference of the IEEE EMBS, Aug. 23-26, 2007, pp. 4251-4254.
Nguyen, T-U. et al., 'A Study of IOS Data Using the aRIC+Ip Model of Respiratory Impedance', 31st Annual International Conference of the IEEE EMBS, Sep. 2-6, 2009, pp. 2875-2878.

\* cited by examiner

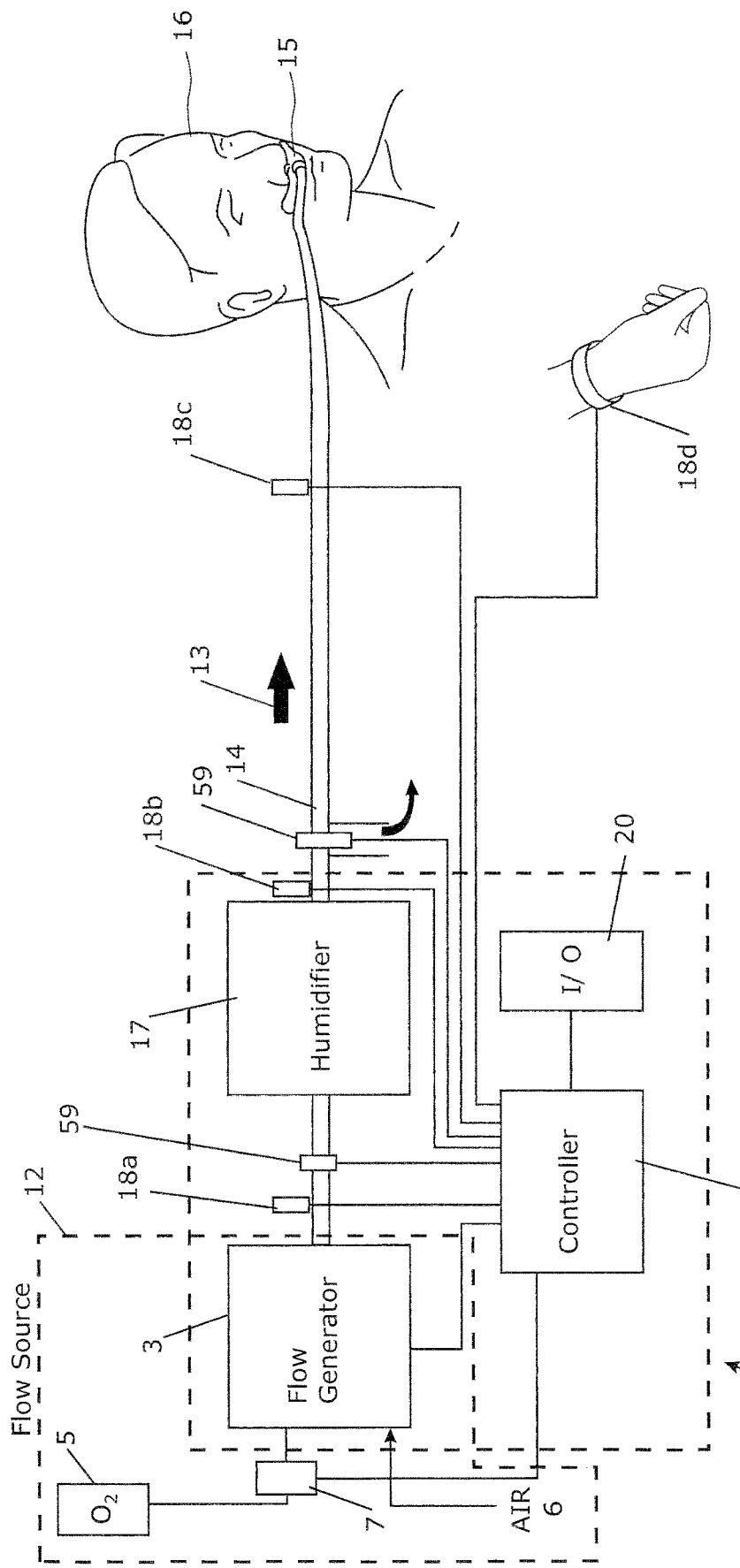
FIGURE 1
FIGURE 1A
FIGURE 1B

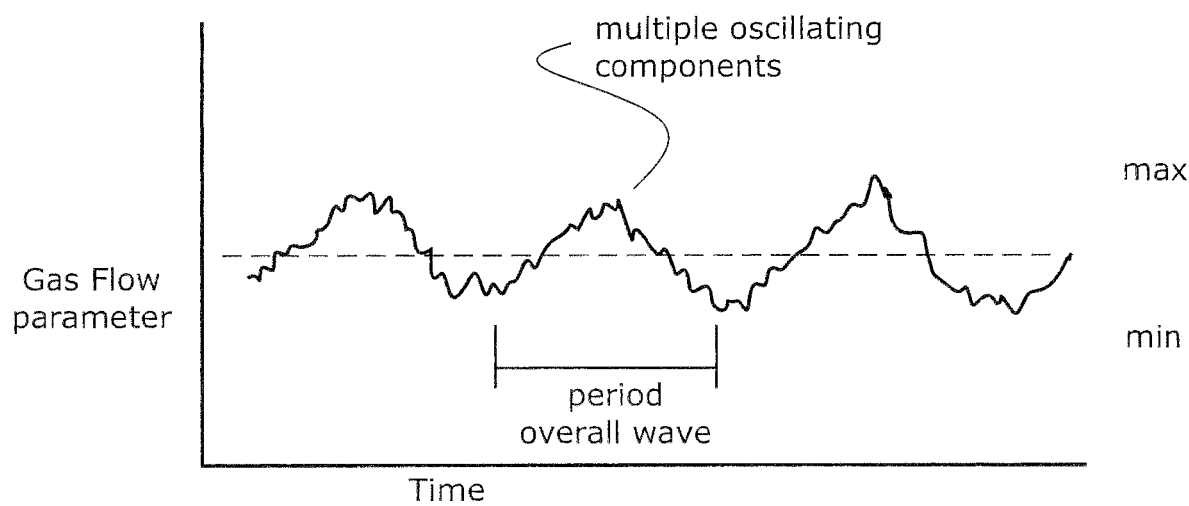
*FIGURE 5E*
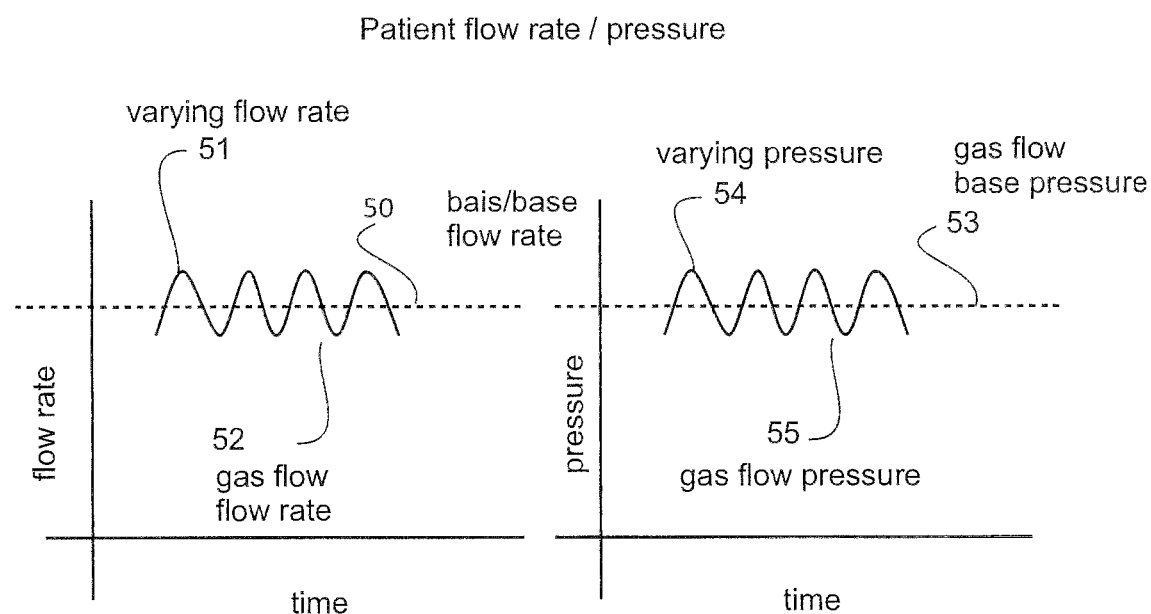
*FIGURE 5F*  *FIGURE 5G*

METHODS AND APPARATUS FOR OXYGENATION AND/OR CO2 REMOVAL

FIELD OF THE INVENTION

The present invention relates to methods and apparatus for oxygenation and/or CO2 removal for a patient, in relation to anaesthesia or more generally medical procedures where respiratory function might be compromised.

BACKGROUND TO THE INVENTION

Patients may lose respiratory function during anaesthesia, or sedation, or more generally during certain medical procedures. Prior to a medical procedure a patient may be pre-oxygenated by a medical professional to provide a reservoir of oxygen saturation, and this pre-oxygenation is generally carried out with a bag and a face mask. Once under general anaesthesia, patients must be intubated to ventilate the patient. In some cases, intubation is completed in 30 to 60 seconds, but in other cases, particularly if the patient's airway is difficult to traverse (for example, due to cancer, severe injury, obesity or spasm of the neck muscles), intubation will take significantly longer. While pre-oxygenation provides a buffer against declines in oxygen saturation, for long intubation procedures, it is necessary to interrupt the intubation process and reapply the face mask to increase the patient's oxygen saturation to adequate levels. The interruption of the intubation process may happen several times for difficult intubation processes, which is time consuming and puts the patient at severe health risk. After approximately three attempts at intubation the medical procedure will be abandoned.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

Disclosed is a method of oxygenation and/or CO2 clearance of a patient during a medical procedure with diminished or risk of diminished respiratory drive comprising operating a flow source to deliver an oscillating gas flow to the patient.

It is therefore an object of one or more of the disclosed embodiments to oxygenation and/or CO2 removal for a patient in relation to medical procedures (including anaesthesia) and/or to at least provide the public with a useful choice.

In the context of this specification "heart activity" is that which may be depicted as a waveform of its electrical impulses or the pulsatile arterial/venous pressure generated by the beating heart. Furthermore, in this specification, cardiogenic oscillations refer to the movement of gas caused by the activity of the heart, and it is understood that references to measuring heart activity include measurements of cardiogenic oscillations, for example by a flow sensor.

In accordance with at least one of the embodiments disclosed herein there is a method of oxygenation and/or CO2 clearance of a patient during a medical procedure with diminished or risk of diminished respiratory drive comprising operating a flow source to deliver an oscillating gas flow to the patient.

In accordance with at least one of the embodiments disclosed herein the pressure and/or flow rate of the gas flow is oscillated.

The gas flow may: oscillates at a frequency between 2 to 200 HZ, has a flow rate amplitude of up to 200 L per min has a pressure amplitude of up to 50 cmH20, and/or has a waveform shape or one or more of: sinusoidal square triangular, and/or saw tooth.

The oscillation may be delivered and/or determined by patient respiratory phase.

The gas flow may be oscillated at a frequency(ies) based on or to match one or more of: patient's heart activity patient's lung's resonant frequency, random noise, patient's chest wall movement, patient's diaphragm muscle, contraction patient's neuron firing, respiratory activity CO2 level.

Also disclosed is a method of oxygenation and/or CO2 clearance of a patient during a medical procedure with diminished or risk of diminished respiratory drive comprising operating a flow source to deliver a constant, varying, oscillating, switching flow of gas flow to the patient.

Also disclosed is an apparatus for oxygenation and/or CO2 clearance of a patient during a medical procedure with diminished or risk of diminished respiratory drive, comprising: a flow source, a controller to control the flow source to provide: an oscillating gas flow to a patient during a medical procedure, and/or a constant, varying, oscillating, switching jet of gas flow to the patient during a medical procedure.

The pressure and/or flow rate of the gas flow may be oscillated.

The gas flow may: oscillates at a frequency between 2 to 200 HZ, has a flow rate amplitude of up to 200 L per min, has a pressure amplitude of up to 50 cmH20, and/or has a waveform shape or one or more of: sinusoidal, square, triangular, and/or saw tooth.

The oscillation may be delivered and/or determined by patient respiratory phase.

The gas flow is oscillated at a frequency(ies) based on or to match one or more of: patient's heart activity, patient's lung's resonant frequency, random noise, patient's chest wall movement, patient's diaphragm muscle contraction, patient's neuron firing.

The gas flow may be delivered by one or more of: a nasal cannula, Endotrachael tube, other anaesthetic equipment.

Further disclosed is a patient interface with nasal prongs with a diameter that is configurable.

The gas flow may be delivered by the patient interface of the configurations described herein, wherein the prongs are configured by the controller.

In accordance with at least one of the embodiments disclosed herein there is an apparatus according to the various embodiments of configurations described herein further comprising a connector for connecting the flow source interchangeably between a patient interface and a large bore needle.

In accordance with at least one of the embodiments disclosed herein there is a system for providing an oscillatory flow of gases that matches the heart beats, comprising: a flow source generator and a controller to influence the flow or parameters or characteristics of the flow such that, in-use, the gases supplied to a user are substantially matched to those of the user's heart beat.

In accordance with at least one of the embodiments disclosed herein there is a method of matching a flow of gases to a user's heart beat, comprising: measuring or determining the user's heart beat and adjusting or controlling the flow of gas from a source being supplied to the user.

In accordance with at least one of the embodiments disclosed herein there is an apparatus for oxygenation and/or $CO_2$ clearance of a patient, comprising: a flow source or a connection for a flow source for providing a gas flow, a gas flow modulator, a controller to control the gas flow, wherein the controller is operable to: receive input relating to heart activity and/or trachea flow of the patient, and control the gas flow modulator to provide a varying gas flow with one or more oscillating components with a frequency or frequencies based on the heart activity and/or trachea flow of the patient.

The apparatus may: comprise a heart activity sensor or has input for receiving input from a heart activity sensor, and/or comprises memory for storing heart activity information, wherein the controller receives input relating to heart activity from the sensor, input and/or memory, and/or comprises a flow sensor or has input for receiving input from a flow sensor.

The apparatus may be an apparatus for providing nasal high flow and/or the apparatus may comprises or be for use with a high flow nasal cannula.

The varying gas flow may have an oscillating flow rate and the controller controls the gas flow modulator to provide the varying gas flow with an oscillating flow rate of: about 375 litres/min to about 0 litres/min, or preferably of about 240 litres/min to about 7.5 litres/min, or more preferably of about 120 litres/min to about 15 litres/min.

The oscillating flow rate may comprise a base flow rate component, wherein the base flow rate is about 375 litres/min to 0 litres/min, or about 150 litres/min to about 0 litres/min, or is preferably about 120 litres/min to about 15 litres/min, or is more preferably about 90 litres/min to about 30 litres/min.

The apparatus may be for use on persons greater than about 30 kg.

The oscillating flow rate may comprise a base flow rate component, wherein the base flow rate is about 0.5 litres/min to about 25 litres/min.

The oscillating flow rate comprises a base flow rate component, wherein the base flow rate is in the range of 0.4 litres/min per patient kilogram to 0.8 litres/min per patient kilogram.

The apparatus may be for use on persons within about 0.3 to 30 kilograms.

The oscillating flow rate may comprise a base flow rate component, wherein the base flow rate is about 8 litres/min for person under about 2 kilograms.

The gas flow modulator may be a flow generator and the flow source comprises the flow generator, the controller being operable to control the flow generator to provide an oscillating gas flow.

The gas flow modulator may be a valve after the flow source, the controller being operable to control the valve to provide an oscillating gas flow.

The controller may be operable to control the gas flow modulator to provide a varying gas flow with one or more oscillating components with a frequency and/or phase based on the heart activity.

The relative phase may be either a) in phase with the heart activity, b) in anti-phase with the heart activity, or c) is an arbitrary phase.

The heart activity may have one or more frequencies, and the controller is operable to control the gas flow modulator to provide an oscillating gas flow with one or more oscillating components with a frequency or frequencies different to those of the heart activity.

The heart activity may have one or more frequencies, and the controller is operable to control the gas flow modulator to provide an oscillating gas flow with one or more oscillating component with a frequency or frequencies corresponding to those of the heart activity.

The varying gas flow may have an oscillating flow rate comprising at least two flow rate components with respective frequencies, wherein a first flow rate component provides bulk gas flow at a frequency corresponding to a breath rate of a patient, and a second flow rate component has a different frequency.

The gas flow modulator may be one or more of: an underwater pressure release valve, oscillatable diaphragm, in-line linear actuator, flow chopper, aerodynamic or mechanical flutter valve, proportional valve (optionally including a proportional valve with a variable size orifice, variable based on an electrical signal).

The gas flow modulator may be before, in or after the flow source.

The gas flow may have an oxygen fraction of 100%, or 30-40% or 40-50% or 60-70% or 80-90% or 90-100%.

The gas flow may have an oxygen fraction of at least about 21% and comprises one or more of nitrous oxide, nitric oxide and/or helium.

The gas flow may be air.

The apparatus may be adapted to provide gas flow to a patient via a patient interface, either non-sealing or sealing.

The apparatus may be adapted to provide gas flow to a patient via a non-sealing cannula.

The apparatus may comprise a humidifier to humidify the gas flow before or after it is oscillated.

The apparatus may additionally comprise one or more sensors for measuring one or more physiological parameters of a patient, and/or one or more inputs for receiving a signal from one or more sensors for measuring physiological parameters of a patient, wherein the one or more physiological parameters are one or more of: heart activity, oxygen saturation, partial pressure of oxygen in the blood, respiratory rate, partial pressure of $CO_2$ in the blood, exhaled $CO_2$.

The varying gas flow may an oscillating flow rate, and the varying gas flow and/or oscillating flow rate have one or more parameters, comprising one or more of: maximum flow rate, minimum flow rate, frequency period, and the varying gas flow and/or oscillating flow rate parameters are set by the controller based on user input and/or automatically from measurements of patient physiological functions and patient physiological parameters.

The controller may be adapted to receive input relating to exhaled $CO_2$ and utilise that to control the gas flow.

In accordance with at least one of the embodiments disclosed herein there is an apparatus for oxygenation and/or $CO_2$ clearance of a patient, during a medical procedure, comprising: a flow source or a connection for a flow source for providing a gas flow, a gas flow modulator, a controller to control the gas flow by controlling the gas flow modulator to provide an varying gas flow with one or more frequencies, wherein during the procedure the patient is apnoeic for at least a portion of the procedure and/or the patient is under anaesthesia causing diminished or risk of diminished respiratory function.

The varying gas flow may have an oscillating flow rate and the controller controls the gas flow modulator to provide the varying gas flow with an oscillating flow rate of: about 375 litres/min to about 0 litres/min, or preferably of about 240 litres/min to about 7.5 litres/min, or more preferably of about 120 litres/min to about 15 litres/min, and/or the oscillating flow rate has one or more frequencies of about 0.1 Hz to about 200 Hz, and preferably about 0.1 Hz to about 3 Hz, and more preferably about 0.5 Hz to about 3 Hz.

The oscillating flow rate may comprise a base flow rate component, wherein the base flow rate is about 375 litres/min to 0 litres/min, or 150 litres/min to about 0 litres/min, or is preferably about 120 litres/min to about 15 litres/min, or is more preferably about 90 litres/min to about 30 litres/min.

The oscillating flow rate may comprise a base flow rate component, wherein the base flow rate is about 0.2 litres/min per patient kilogram to about 2.5 litres/min per patient kilogram; and preferably is about 0.25 litres/min per patient kilogram to about 1.75 litres/min per patient kilogram; and more preferably is about 0.3 litres/min per patient kilogram to about 1.25 litres/min or about 1.5 litres/min per patient kilogram The apparatus may be for use on persons greater than about 30 kg.

In accordance with at least one of the embodiments disclosed herein there is a method for oxygenation and/or CO2 clearance of a patient, during a medical procedure, comprising: delivering a varying gas flow via a nasal interface to the patient by varying the gas flow at one or more frequencies during the procedure while the patient is apnoeic for at least a portion of the procedure and/or the patient is under anaesthesia causing diminished or risk of diminished respiratory function.

The varying gas flow may have an oscillating flow rate of: about 375 litres/min to about 0 litres/min, or preferably of about 240 litres/min to about 7.5 litres/min, or more preferably of about 120 litres/min to about 15 litres/min and/or the oscillating flow rate has one or more frequencies of about 0.1 Hz to about 200 Hz, and preferably about 0.1 Hz to about 3 Hz, and more preferably about 0.5 Hz to about 3 Hz.

The oscillating flow rate may comprise a base flow rate component, wherein the base flow rate is about 375 litres/min to 0 litres/min, or 150 litres/min to about 0 litres/min, or is preferably about 120 litres/min to about 15 litres/min, or is more preferably about 90 litres/min to about 30 litres/min.

The oscillating flow rate may comprise a base flow rate component, wherein the base flow rate about 0.2 litres/min per patient kilogram to about 2.5 litres/min per patient kilogram; and preferably is about 0.25 litres/min per patient kilogram to about 1.75 litres/min per patient kilogram; and more preferably is about 0.3 litres/min per patient kilogram to about 1.25 litres/min or about 1.5 litres/min per patient kilogram.

The method may be for a patient greater than about 30 kg.

The method may be for providing gas flow prior to the medical procedure.

The gas flow may have a flow rate, wherein a first flow rate provided prior to the medical procedure and a second flow rate is provided during the medical procedure, and optionally a third flow rate after the medical procedure.

The second flow rate may be greater than the first flow rate; and/or the third flow rate may be less than the second flow rate.

The method may have: the first flow rate being about 15 L/min to about 90 L/min, or about 20 L/min to about 80 L/min, or about 25 L/min to about 60 L/min, or about 30 L/min to about 50 L/min, or about 40 L/min to about 30 L/min; and/or second flow rate being about 20 L/min to about 150 L/min, or about 40 L/min to about 120 L/min, or about 50 L/min to about 100 L/min, or about 60 L/min to about 80 L/min, or about 70 L/min, or about 60 L/min; and/or the third flow rate is less than about 90 L/min, or less than about 70 L/min, or less than about 50 L/min, or less than about 40 L/min, or less than about 20 L/min, or about 40 L/min, or about 30 L/min.

The controller may be adapted to receive input relating to exhaled CO2 and utilise that to control the gas flow.

The apparatus may be an apparatus for providing nasal high flow and/or the apparatus comprises or is for use with a high flow nasal cannula.

The method may comprise delivering nasal high flow therapy.

In accordance with at least one of the embodiments disclosed herein there is an apparatus for promoting gas exchange with a patient, comprising: a flow source or connection for a flow source for providing a gas flow, a gas flow modulator, a controller to control the gas flow, and wherein the controller is operable to control the gas flow modulator to provide a varying gas flow with a base gas flow component and at least one oscillating gas flow component with one or more frequencies of about 0.1 Hz to about 3 Hz.

The one or more oscillating gas flow components may have one or more frequencies of about 0.3 Hz to about 3 Hz.

The varying gas flow may have an oscillating flow rate and the controller controls the gas flow modulator to provide the varying gas flow with an oscillating flow rate of: about 375 litres/min to about 0 litres/min, or preferably of about 240 litres/min to about 7.5 litres/min, or more preferably of about 120 litres/min to about 15 litres/min.

The oscillating flow rate may comprise a base gas flow component, wherein the base flow rate is about 375 litres/min to 0 litres/min, or about 150 litres/min to about 0 litres/min, or is preferably about 120 litres/min to about 15 litres/min, or is more preferably about 90 litres/min to about 30 litres/min.

The oscillating flow rate may comprise a base gas flow component, wherein the base flow rate about 0.2 litres/min per patient kilogram to about 2.5 litres/min per patient kilogram; and preferably is about 0.25 litres/min per patient kilogram to about 1.75 litres/min per patient kilogram; and more preferably is about 0.3 litres/min per patient kilogram to about 1.25 litres/min or about 1.5 litres/min per patient kilogram.

The oscillating flow rate may comprise at least one oscillating flow rate component, wherein each oscillating flow rate is about 0.05 litres/min per patient kilogram to about 0.5 litres/min per patient kilogram; and preferably about 0.12 litres/min per patient kilogram to about 0.4 litres/min per patient kilogram; and more preferably about 0.12 litres/min per patient kilogram to about 0.35 litres/min per patient kilogram.

The apparatus may be for use on persons greater than about 30 kg.

The oscillating flow rate may comprise a base gas flow component, wherein the base flow rate component is about 0.5 litres/min to about 25 litres/min.

The oscillating flow rate may comprise a base gas flow component, wherein the base flow rate component in the range of 0.4 litres/min per patient kilogram to 0.8 litres/min per patient kilogram.

The oscillating flow rate may comprise at least one oscillating flow rate component, wherein each oscillating flow rate is in the range of 0.05 litres/min per patient kilogram to 2 litres/min per patient kilogram; and preferably in the range of 0.1 litres/min per patient kilogram to 1 litres/min per patient kilogram; and more preferably in the range of 0.2 litres/min per patient kilogram to 0.8 litres/min per patient kilogram.

The apparatus may be for use on persons within about 0.3 to 30 kilograms.

The base gas flow component may be a base flow rate component in the range, wherein the base flow rate is about 8 litres/min for person under about 2 kilograms.

The oscillating gas flow may have a plurality of oscillating gas flow components at a plurality of frequencies.

The apparatus may have one of more of the frequencies is about 0.1 HZ to about 3 Hz.

The apparatus may have oscillating gas flow has a period of about 0.3 to about 10 s.

The controller may be adapted to receive input relating to exhaled CO2 and utilise that to control the gas flow.

The apparatus wherein: if the resting heart rate is about 40 to about 100 bpm, the oscillation gas flow component has a frequency of about 0.67 to about 1.67 Hz, and if the heart rate is about 30 to about 180 bpm the oscillation gas flow component has a frequency of about 0.67 to about 0.5 to about 3 Hz).

The apparatus may be an apparatus for providing nasal high flow and/or the apparatus may comprises or be for use with a high flow nasal cannula The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

"high flow therapy" may refer to the delivery of gases to a patient at a flow rate of between about 5 or 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. For example, according to those various embodiments and configurations described herein, a flow rate of gases supplied or provided to an interface or via a system, such as through a flowpath, may comprise, but is not limited to, flows of at least about 5, 10, 20, 30, 40, 50, 60, 70, 80, 90, 100, 110, 120, 130, 140, 150 L/min, or more, and useful ranges may be selected between any of these values (for example, about 40 to about 80, about 50 to about 80, about 60 to about 80, about 70 to about 100 L/min, about 70 to 80 L/min).

The invention consists in the foregoing and also envisages constructions of which the following gives examples only.

BRIEF DESCRIPTION OF THE DRAWINGS

Preferred embodiments of the invention will be described by way of example only and with reference to the drawings, in which:

FIG. 1 illustrates an apparatus/system for oxygenating a patient and/or CO2 removal with high flow gas in relation to anaesthesia.

FIG. 1A schematically illustrates a nasal cannula with adjustable diameter prongs.

FIG. 1B illustrates a large bore needle for flow.

FIGS. 5A to 5G illustrate a varying gas flow with oscillating parameters, such as pressure and flow rate.

DETAILED DESCRIPTION OF PREFERRED EMBODIMENTS

1. Overview of Embodiments and Examples

Figure 1C:
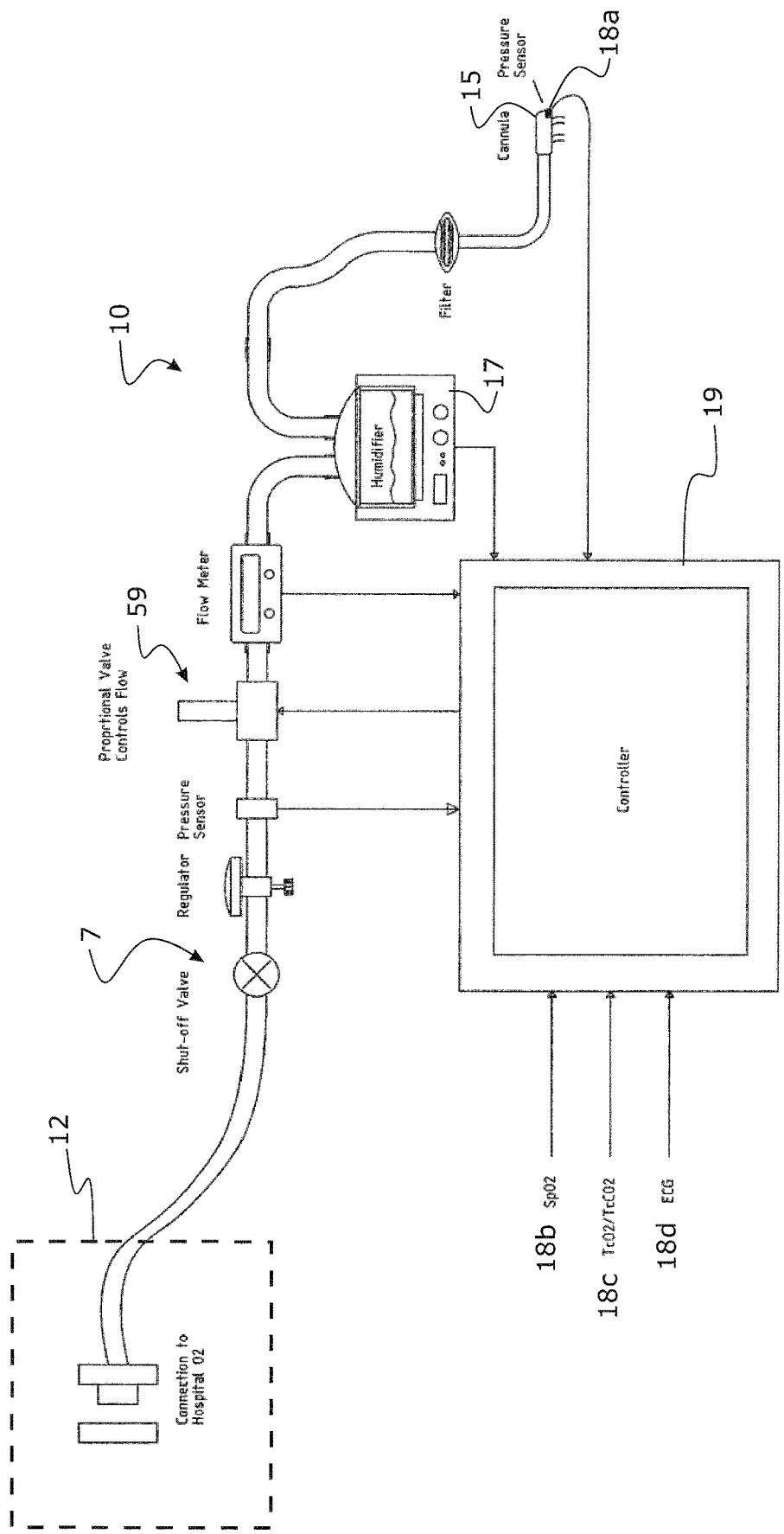
FIG. 1C illustrates a variation of an apparatus/system for oxygenating a patient and/or CO2 removal with high flow gas in relation to anaesthesia.

In general terms, apparatus and methods described herein relate to flow therapy methods and apparatus that assist oxygenation and/or CO2 removal in a respirating patient (respirating referring to either spontaneous or assisted respiration), and preferably during anaesthesia, and/or during resuscitation, and/or at any medical procedure or other time that assistance is required. Flow therapy (also termed high flow therapy) relates to apparatus and methods that deliver relatively high flows of gas to assist a patient respiration.

Some apparatus and methods described herein vary the gas flow to generate a varying gas flow with gas flow oscillations. This assists with CO2 removal, and also can assist with oxygenation of a patient. For example, parameter(s) of the delivered varying high flow of gas are adjusted to oscillate those parameter(s) to provide a varying gas flow. For example, the pressure and/or flow rate of a delivered high flow of gas is oscillated. In some embodiments, the oscillations are based on (such as correspond to, or are synchronised with) or are otherwise determined using, one or more of: the resonant frequency of patient lungs and/or chest wall, patient cardiogenic pulsations, patient diaphragm contraction, patient brain activity, patient breathing rate, partial pressures of $CO_2$ or $O_2$, exhaled $CO_2$ or the like and also using other suitable sensed physiological parameters. Such methods and apparatus can be utilised when the patient is apnoeic or otherwise has diminished respiratory function, either during a medical procedure or otherwise. To provide additional efficacy, optionally the patient's oxygenation requirements can be determined and gas flow oscillations can be adjusted accordingly to improve oxygenation, and/or the patient's $CO_2$ can be sensed to assist with determining how to vary the gas flow with gas flow oscillations to remove $CO_2$. As will be described, it has been determined that providing gas flow oscillations in a varying high flow gas flow assists with/improves $CO_2$ removal. Apnoea can occur due to, for example, respiratory depression from anaesthesia (or a variety of other causes), such that the patient stops breathing.

A continuous supply of oxygen is essential to sustain healthy respiratory function during medical procedures (such as during anaesthesia) where respiratory function might be compromised. When this supply is compromised, hypoxia and/or hypercapnia can occur. During medical procedures such as anaesthesia, the patient is monitored to ensure this does not happen. If oxygen supply and/or $CO_2$ removal is compromised the clinician stops the medical procedure and facilitates oxygen supply and/or $CO_2$ removal. This can be achieved for example by manually ventilating the patient through self inflating bag-valve-masks.

In other methods and apparatus described herein, the apparatus and/or methods can adjust parameter(s) of high flow of gas (e.g. pressure and/or flow rates) in a non-oscillatory manner to be delivered/provided to a patient to assist with oxygenation and/or $CO_2$ removal during medical procedures. Patient oxygenation requirements can be determined to assist.

1.1 Oxygenation and/or $CO_2$ Removal Using Varying Gas Flow

In methods and apparatus described herein, a varying gas flow can be provided, the varying gas flow being oscillated to create an oscillating gas flow comprising a base gas flow component and one or more oscillating gas flow components. The varying gas flow with gas flow oscillations would be useful when a patients' respiratory drive is compromised or at least reduced, whether this is before, during or after a medical procedure or in any other situation. The varying gas flow with oscillating components predominantly assists to remove $CO_2$ from a respiring patient. $CO_2$ removal can be useful when a patient is apnoeic, or when a patient has diminished respiratory function, such as when sedated or descending into or coming out of anaesthesia. During these events, a patient's respiratory function might not be good enough to sufficiently clear $CO_2$ unassisted. There can be other situations where $CO_2$ removal assistance is desirable also. As will be described, it has been determined that providing oscillations in a varying gas flow assists with/improves $CO_2$ removal.

Varying the gas flow with oscillating components can also help to oxygenate the patient both directly by assisting the delivery of oxygen and indirectly by removing $CO_2$.

Particular embodiments and examples of apparatus/systems and methods are described for altering the parameters of high gas flow oxygenation. At least some of those embodiments can assist $CO_2$ removal from a patient by gas delivery, for example during a medical procedure (such as anaesthesia). Embodiments described are particularly (but not solely) useful for patients that are not spontaneously breathing. When a patient is not spontaneously breathing, their ability to oxygenate and clear $CO_2$ can be diminished. Some embodiments relate to apparatus and methods of oxygenation and/or $CO_2$ removal. In general terms, the embodiments relate to methods and apparatus of utilising a high flow source of gas (such as oxygen and/or other gas mixes) for oxygenating a patient, and/or methods and apparatus that facilitate removal of $CO_2$.

1.2 Oxygenation and/or $CO_2$ Removal Using High Gas Flow

In a method and apparatus described herein, (high) flow gas (e.g. oxygen or a mix of oxygen and one or more other gases) can be delivered to a patient to reduce the risk of hypoxia. This high flow gas can be provided during a medical procedure prior to anaesthesia (pre-oxygenation) while the patient is still (spontaneously) breathing, or during anaesthesia (where a patient may not be spontaneously breathing and needs assistance), including when the patient might be apnoeic. The use of gas flow provides hands-free oxygenation, unlike current methods, allowing an anaesthesiologist or other clinicians to concentrate their efforts on the medical procedure itself, without the patient de-saturating. The gas flow might be provided at a constant flow rate to deliver the "dose" of oxygen required (patient oxygen requirement) to avoid hypoxia. This dose can also be referred to as the required "therapy" or "support". The dose relates to the one or more parameters of the high flow gas being delivered, and an optimal or required dose relates to the high flow gas parameters that provide a patient with their oxygen requirements. For example, the parameters might be (although are not limited to) one or more of:

flow rate of gas (such as flow rate of oxygen and including oscillatory flow)
volume of gas delivered
pressure of gas
composition and/or concentration of gas.

1.3 Determining Oxygenation Requirements

In a method and apparatus described herein, it can be desirable to determine the oxygen requirements, and adjust (either continuously or periodically) the gas flow parameters accordingly to ensure oxygenation and/or $CO_2$ removal to the required level. In general terms, the dose/oxygen requirements are determined before anaesthesia and/or during (e.g. thorough continuous or periodic monitoring) anaesthesia, as well as afterward, including an extubation period; and then the parameters of the high gas flow are altered accordingly (manually or automatically) to provide the required oxygenation to the patient. It should be noted that reference to "anaesthesia" and its stages throughout this specification can refer to actual anaesthesia, and the period prior to anaesthesia (such as the pre-oxygenation stage).

2. First Embodiment of Apparatus/Method for Assisting with $CO_2$ Removal and/or Oxygenation 2.1 Apparatus for Assisting with $CO_2$ Removal and/or Oxygenation Using Varying Gas Flow FIG. 1 shows a system/apparatus 10 for delivering a varying gas flow with oscillations (oscillating gas flow) to a patient to assist with $CO_2$ removal, and which can also to assist with oxygenation, in the situations described above.

The system/apparatus 10 could be an integrated or a separate component based arrangement, generally shown in the dotted box 11 in FIG. 1. In some configurations the system 10 could be a modular arrangement of components. Hereinafter it will be referred to as system, but this should not be considered limiting.

The apparatus comprises a flow source 12 for providing a high flow gas such as oxygen, or a mix of oxygen and one or more other gases. Alternatively, the apparatus can have a connection for coupling to a flow source. As such, the flow source might be considered to form part of the apparatus 10 or be separate to it, depending on context, or even part of the flow source forms part of the apparatus, and part of the flow source fall outside the apparatus.

The flow source could be an in-wall supply of oxygen, a tank of oxygen, a tank of other gas and/or a high flow therapy apparatus with a blower/flow generator 3. FIG. 1 shows a flow source with a flow generator 3, with an optional air inlet 6 and optional connection to an O2 source 5 (such as tank or O2 generator) via a shut off valve and/or regulator and/or other gas flow control (all represented as 7), but this is just one option. In an alternative in FIG. 1C, there is no flow generator, but rather the flow source 12 is an in-wall O2 or blended O2/Air supply, optionally with a flow meter. A shut off valve, regulator and pressure sensor arrangement 7 is also shown. The description from here can refer to either embodiment. The flow source could be one or a combination of a flow generator, O2 source, air source as described. Any valves associated with the flow source 12 could be considered part of the flow source, or external to it, depending on context. The flow source is shown as part of the system 10, although in the case of an external oxygen tank or in-wall source, it may be considered a separate component, in which case the apparatus has a connection port to connect to such flow source. The flow source 12 provides a (preferably high) flow of gas 13 that can be delivered to a patient 16 via a delivery conduit 14, and patient interface 15 (such as a (non-sealing) nasal cannula or sealing nasal mask). The flow source could provide a base gas flow rate of between, e.g., 0.5 litres/min and 375 litres/min, or any range within that range, or even ranges with higher or lower limits. Details of the ranges and nature of flow rates will be described later.

A humidifier 17 can optionally be provided between the flow source and the patient to provide humidification of the delivered gas. One or more sensors 18a, 18b, 18c, 18d, such as flow, oxygen fraction, pressure, humidity, temperature or other sensors can be placed throughout the system and/or at, on or near the patient 16. Alternatively, or additionally, sensors from which such parameters can be derived could be used. In addition, or alternatively, the sensors 18a-18d can be one or more physiological sensors for sensing patient physiological parameters such as, heart rate, oxygen saturation, partial pressure of oxygen in the blood, respiratory rate, partial pressure of CO2 in the blood. Alternatively or additionally, sensors from which such parameters can be derived could be used. Other on patient sensors could comprise EEG sensors, torso bands to detect breathing, and any other suitable sensors. In some configurations the humidifier may be optional or it may be preferred due to the advantages of humidified gases helping to maintain the condition of the airways. One or more of the sensors might form part of the apparatus, or be external thereto, with the apparatus having inputs for any external sensors.

The output from the sensors is sent to a controller to assist control of the apparatus, including among other things, to vary gas flow to provide an oscillating gas flow.

As an example, the sensors can comprise a pulse oximeter 18d on the patient for determining the oxygen saturation the blood. The pulse oximeter provides an analogue or digital electrical signal for the controller 19.

As another example, the partial pressure of oxygen in the blood could be sensed by using a transcutaneous oxygen monitor (sensor). The oxygen sensor measures the concentration of oxygen and this reading is corrected for temperature to produce an estimated partial pressure for oxygen in the blood. The instrument electronic system provides an analogue or digital signal which directly indicates the partial pressure of blood oxygen, and which is connected to the controller 19.

As another example, respiratory rate could be sensed using respiratory inductance plethysmography (RIP) with an analogue or digital signal that is connected to the controller 19.

As another example, the partial pressure of CO2 in the blood can be sensed using a transcutaneous monitor with an analogue or digital signal that is connected to the controller 19.

As another example, exhaled CO2 is sensed using an exhaled CO2 sensor. The CO2 partial pressure reading is transmitted to the controller in either analogue or digital form.

Another example is a heart activity sensor for sensing patient heart activity. The controller 19 is connected to receive input from the heart activity sensor (such as a sensor output signal) relating to heart activity of the patient. This enables the controller to control gas flow based on the received input from the heart activity sensor.

A controller 19 is provided, which is coupled to the flow source 12, humidifier 17 and sensors 18a-18d. It controls these and other aspects of the apparatus to be described below.

The apparatus also comprises one or more gas flow modulators 59, which can be used to modulate (that is, varying, modify, adjust or otherwise control parameters of the gas flow). Each gas flow modulator can be provided in the flow source (and the flow source itself can be a gas flow modulator), after the flow source and before the humidifier, after the humidifier, and/or in any other suitable place in the apparatus to modulate gas flow path. Examples are shown in FIGS. 1 and 1B, but not all are required, and their position and number can vary based on the requirements of the system. Other examples are described later with reference to FIGS. 6 to 9. Types of gas flow modulators will be described later.

The controller 19 can operate the flow source to provide the delivered flow of gas. It can also operate the gas flow modulator(s) (including the flow source) to control the flow, pressure, volume and/or other parameters of gas provided by the flow source based on feedback from sensors, or optionally without feedback (e.g. using default settings). The controller can also control any other suitable parameters of the flow source to meet oxygenation requirements and/or CO2 removal. The controller 19 can also control the humidifier 17 based on feed-back from the sensors 18a-18d. Using input from the sensors, the controller can determine oxygenation requirements and control parameters of the flow source, gas flow modulator(s) and/or humidifier as required. An input/output interface 20 (such as a display and/or input device) is provided. The input device is for receiving information from a user (e.g. clinician or patient) that can be used for determining oxygenation requirements and/or CO2 detection.

The apparatus can also be operated to determine dose/oxygenation requirements (hereinafter "oxygen requirements") of a patient for/in relation to anaesthesia (that is, the oxygen requirements pre-anaesthesia during a pre-oxygenation phase and/or the oxygen requirements during anaesthesia—which might include when the patient is apnoeic or when the patient is breathing), as well as after such a procedure, which may include the extubation period. The system/apparatus 10 is also configured to adjust and provide high flow gas to a patient for the purposes of anaesthesia, and adjust the parameters of the high flow gas (such as pressure, flow rate, volume of gas, gas composition) delivered to the patient as required to meet oxygenation requirements.

2.2 $CO_2$ Removal and/or Oxygenation Using Varying Flow

Use of the apparatus will now be described.

A high flow gas delivered by a high flow therapy method or apparatus comprises various components with one or more parameters that can be adjusted, including being adjusted to oscillate. Each parameter might be adjusted independently, or in dependence on other parameters. This provides a varying gas flow (varying gas flow parameters). The varying gas flow (with oscillations) assists $CO_2$ removal and can assist oxygenation.

In one embodiment, the controller 19 is configured to vary the gas flow to create an oscillating gas flow to improve $CO_2$ removal (and optionally improve oxygenation). This could be used either during pre-oxygenation or during anaesthesia, or during any other medical procedure where the patient is apnoeic or otherwise where respiratory function might be diminished. To generate the oscillating gas flow, a parameter or parameters of the delivered gas flow are oscillated, with one or more frequencies, amplitudes and/or phases. For example, and typically, the flow rate of the gas flow is oscillated with one or more frequencies (including a phase and amplitude), which in turn oscillates the pressure generated by the delivered gas flow. However, other parameters could be oscillated—for example the pressure of the gas flow could be oscillated. The oscillating gas flow can comprise one or more oscillating components, all of different frequencies, amplitude and phase. The overall oscillating gas flow can be represented as a (summed) waveform, with a waveform shape comprising the various (summed) oscillating components. The nature of the varying gas flow is now described with reference to FIGS. 5A to 5D. The varying gas flow has one or more parameters, including but not limited to, a flow rate (flow rate parameter) and a pressure (pressure parameter). Each varying gas flow parameter (and the gas flow overall) comprises a base component, and one or more oscillating components which together combine (to create a summed waveform or signal). The varying gas flow overall as a result might also oscillate, and oscillation can refer to oscillation of gas flow components, or the overall gas flow. The varying gas flow/gas flow parameters can be represented as one or more waveforms (such as a flow rate waveform and a pressure waveform), with the various components making up the waveform shape, such as in FIG. 5E. The waveform itself may oscillate, and due to the combination of the components will have a waveform shape due to those components. It will be appreciated that the components could be represented or considered as sinusoidal Fourier components, although this is not essential. In this case, the base component would be a fundamental frequency, or DC/bias flow component.

Typically, the apparatus 10 is controlled to generate a varying gas flow with an oscillating flow rate, which results in an oscillating gas flow pressure. The remaining description for FIGS. 5A to 5E will be described in that context. However, this is not essential and it will be appreciated that instead the apparatus could be controlled to oscillate the gas flow pressure, or other gas flow parameter.

Figure 5A:
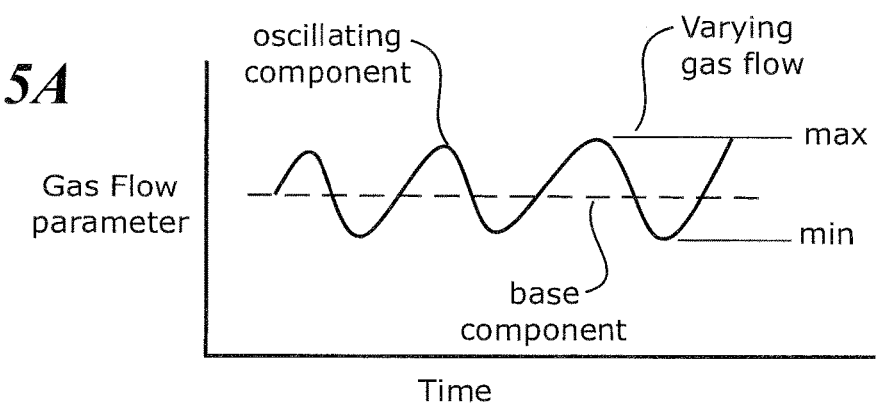
Figure 5B:
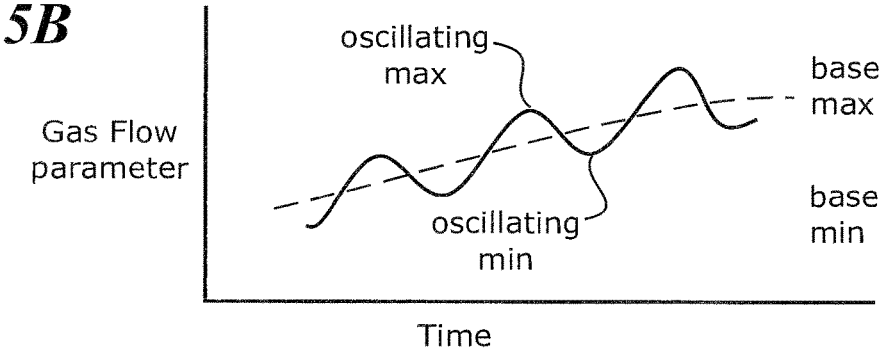
Figure 5C:
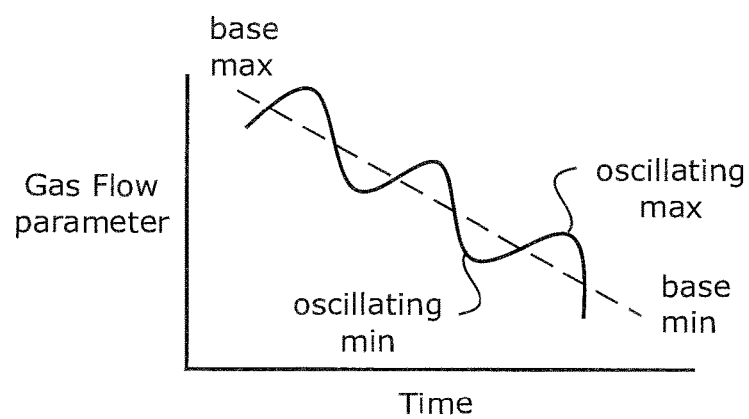
Figure 5D:
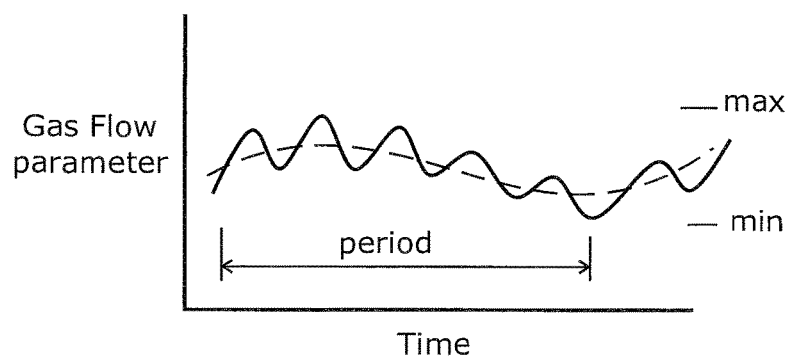

The base flow rate component of a varying gas flow is typically constant (see FIG. 5A), but it could also vary, such as (linear or otherwise) ramping up (See FIG. 5B) or down (see FIG. 5C), or varying in a (relatively slow) oscillatory manner (see FIG. 5D). Oscillation of the base flow rate, if at all, is generally at a very low frequency. Where the base flow rate varies, it can have a maximum and minimum magnitude (amplitude) that it varies between. Likewise, the base pressure component of a varying gas flow is typically constant (See FIG. 5A), but it could also vary, such as (linear or otherwise) ramping up (See FIG. 5B) or down (see FIG. 5C), or varying in a (relatively slow) oscillatory manner (See FIG. 5D). Oscillation of the base pressure, if at all, is generally at a very low frequency. Where the base pressure varies, it can have a maximum and minimum magnitude (amplitude) that it varies between. Other gas flow parameters could vary in a similar manner.

The base flow rate component of a varying gas flow can be summed with/modulated with (e.g. varied, modified, adjusted, or otherwise controlled etc.) or otherwise combined with the one or more (relatively high frequency) oscillatory flow rate components each with a frequency to produce varying gas flow (that may itself oscillate). One oscillatory component summed with the base component is shown in FIGS. 5A to 5D, but more oscillatory components are possible (such as shown in FIG. 5E and described soon). Each oscillatory flow rate component has a frequency that is relatively high compared to any slow oscillatory variation of the base flow rate. Each oscillatory component has a maximum and minimum magnitude (amplitude). Each oscillatory component also has a phase. Likewise, the base pressure component of a varying gas flow will be modulated with/summed with or otherwise combined with one or more (relatively high frequency) oscillatory pressure components to produce an oscillating varying gas flow. Each oscillatory pressure component has a frequency that is relatively high compared to any oscillatory variation of the base flow rate. Each oscillatory component has a maximum and minimum magnitude (amplitude). Each oscillatory component also has a phase.

FIG. 5E shows an example of a general case varying gas flow with a base flow component (e.g. flow rate or pressure) and plurality of oscillating gas flow components (e.g. flow rate or pressure), each of which combine together to provide a varying gas flow (with a waveform shape) with an overall period/oscillation.

Generally herein, reference to an oscillatory component or the like will refer to the high frequency component, not a base component, although it will be appreciated that all such components can be oscillatory. Hereinafter, references to oscillations will be references to oscillations of pressure and/or flow rate as context allows, but this should not be considered limiting and oscillation of other parameters might be possible. Reference to oscillation can also refer to an oscillation with more than one component and frequency.

As an example, and referring to FIGS. 5E, 5F, the controller 19 varies (by controlling the apparatus) the gas flow flow rate 13 from the flow source 12 around a base or bias flow rate 50 (bias in the sense of an offset from zero, equivalent to a DC bias analogy). This provides a (preferably high frequency 51) oscillating gas flow 52 around a (preferably although not necessarily constant) base flow rate 50 that assists with oxygenation and/or $CO_2$ removal. As an alternative or additionally, the gas flow base pressure 53 is modified by an oscillating pressure 54 to provide an oscillating gas flow pressure 55. The pressure might be oscillated directly, or indirectly as a result of oscillating flow rate.

As an example, the frequency of the oscillating component could be 2 to 250 Hz, although the frequency could fall outside this range. More preferably the frequency is about 100 Hz or less, as this is avoids damping issues in the circuit. Where there are multiple oscillating components, each can be in the range above. Other frequencies are possible, as described elsewhere herein. For example, the frequency preferably could be about 0.1 Hz to about 3 Hz.

The frequency or frequencies can be chosen based on a physiological parameter. For example, in the case of basing the frequency on heart activity, frequencies will be around those of heart activity frequencies which are generally below 250 Hz. More preferably, the frequency(ies) is/are about 4 Hz or less and more preferably about 2 Hz or less for a child and about 1 Hz or less for an adult. More preferably, the frequency may be about 0.1 Hz to 3 Hz, or 0.3 Hz to 3 Hz. In either option, the oscillation/variation might not have a single frequency, but might comprise multiple (including a range of) frequencies (with associated phases and amplitudes)—see e.g. FIG. 5E. It will be appreciated that the disclosure herein could relate to any sort of flow rate/pressure or other parameter variation/oscillation with one or more frequencies. Reference in this specification to an oscillation frequency should not be considered limiting and should be considered to cover oscillation comprising two or more frequencies, and might also comprise phase/amplitude information.

The varying gas flow flow rate can have the following non-limiting examples of values. These are made with reference to FIGS. 5A to 5G Flow rate values for an overall combined/summed waveform will be described first—see, e.g. FIG. 5E. This is one or more oscillating components summed together with the base component. The overall (oscillating) waveform has a peak flow rate (amplitude), a trough flow rate (amplitude) and an instantaneous flow rate and a period. This gas flow waveform can have an instantaneous flow rate of about 375 litres/min to about 0 litres/min, or preferably of about 240 litres/min to about 7.5 litres/min, or more preferably of about 120 litres/min to about 15 litres/min. The overall waveform can have a peak (maximum) flow rate of about 375 litres/min to about 0.5 litres/min, or preferably of about 240 litres/min to about 30 litres/min, or more preferably of about 120 litres/min to about 60 litres/min. The overall waveform can have a trough (minimum) flow rate of about 240 litres/min to about 0 litres/min, or preferably of about 120 litres/min to 7 about 0.5 litres/min, or more preferably of about 60 litres/min to about 15 litres/min. The frequency can be about 0.1 Hz to 3 HZ, or 0.3 Hz to about 3 Hz.

The base component (see FIGS. 5A to 5G), has an instantaneous, maximum and minimum flow rate (amplitude). The base component can have an instantaneous flow rate of about 375 litres/min to 0 litres/min, or 150 litres/min to about 0 litres/min, or preferably of about 120 litres/min to about 15 litres/min, or more preferably of about 90 litres/min to about 30 litres/min. If the base component varies (e.g. ramps), the component can have a maximum flow rate of about 150 litres/min to about 0 litres/min, or preferably of about 120 litres/min to about 15 litres/min, or more preferably of about 90 litres/min to about 30 litres/min. If the base component varies (e.g. ramps), the component can have a minimum flow rate of about 150 litres/min to about 0 litres/min, or preferably of about 120 litres/min to about 15 litres/min, or more preferably of about 90 litres/min to about 30 litres/min. In one example, the base component is 30 litres/min to 105 litres/min, but could be 50 litres/min to 120 litres/min for an adult with BMI>40. The maximum and minimum flow rates can still fall within the instantaneous flow rate range, and the instantaneous flow rate range can still fall within the overall waveform flow rate range.

Each oscillating component has an instantaneous, maximum and minimum flow rate (amplitude), frequency and/or phase. The amplitude of an oscillating component might be defined as a relative amplitude, for example with reference to the base component, or it might be defined as an absolute amplitude, or both. Each oscillating component can have an instantaneous flow rate of about 375 litres/min to 0 litres/min, or 150 litres/min to about 0 litres/min, or preferably of about 240 litres/min to about 7.5 litres/min, or more preferably of about 120 litres/min to about 15 litres/min.

The oscillating component can have a maximum flow rate of about 375 litres/min to about 0.5 litres/min (or about 270 litres/min to about 0.25 litres/min relative to the base component), or preferably of about 270 litres/min to about 15 litres/min (or about 120 litres/min to about 0.5 litres/min relative to the base component), or more preferably of about 150 litres/min to about 30 litres/min (or about 60 litres/min to about 10 litres/min relative to the base component). The oscillating component can have a minimum flow rate of about 370 litres/min to about 0.5 litres/min (or about 270 litres/min to about 0.25 litres/min relative to the base component), or preferably of about 240 litres/min to about 15 litres/min (or about 120 litres/min to about 5 litres/min relative to the base component), or more preferably of about 150 litres/min to about 30 litres/min (or about 60 litres/min to about 10 litres/min relative to the base component).

The difference between the peak and the trough (peak to peak flow rate) can be a flow rate of about 240 litres/min to 0.5 litres/min, or preferably 120 litres/min to about 5 litres/min, or more preferably of about 60 litres/min to about 10 litres/min, or alternatively about 0 to about 100 litres/min, or about 40 litres/min to 70 litres/min. The maximum and minimum flow rates can still fall within the instantaneous flow rate range, and the instantaneous flow rate range can still fall within the overall waveform flow rate range. The frequency of an oscillating component can be about 0 to about 200 Hz, or preferably about 0.1 Hz to about 20 Hz, or more preferably about 0.5 Hz to about 3 Hz, and more preferably about 0.1 Hz to about 3 Hz. The phase can be about 0 to about 360 degrees or preferably about 0 to about 270 degrees, or more preferably about 0 to 180 degrees.

In more general terms, the instantaneous flow rate of gases at any point of operation supplied or provided to an interface or via a system, such as through a flow path, may comprise, but is not limited to, flows of 15 litres/min to 150 litres/min and up to 375 litres/min, and optionally at least about 40, 50, 60, 70, or 80 L/min, or more, and useful ranges may be selected between any of these values (for example, about 40 to about 80, about 50 to about 80, about 60 to about 80, about 70 to about 80 L/min, or any other subrange of 15 litres/min to 120 Litres/min, or even up to 150 litres/min or above).

For example, the base flow range would result in min/max flow of about 8 to about 100 L/min and about 30 to about 375 L/min for patients of 40 kg and 150 kg respectively. More preferably, the max/min flow rate is about 15 litres/min to 250 litres/min and more preferably 15 litres/min to 70 litres/min.

For premature/infants/paediatrics (with body mass in the range of about 1 to about 30 kg) the base flow can be set to 0.4-8 L/min/kg with a minimum of about 0.5 L/min and a maximum of about 25 L/min. For patients under 2 kg maximum flow is set to 8 L/min. The oscillating flow is set to 0.05-2 L/min/kg with a preferred range of 0.1 L/min/kg and another preferred range of 0.2-0.8 L/min/kg.

The table below illustrates the maximum and minimum flow rates for 40 kg and 150 kg patients respectively (those are somewhat outside the normal mass distribution where the mean for females/males in the US is about 75/85 kg respectively, 2004 survey). The flow rates noted are set so that in the normal ranges, a 150 kg patient can get 30 L/min pre-oxygenation and a very light patient (40 kg) can get ~50% over the typical 70 litres/min flow rate. In the case of oscillating flow rates, the minimum oscillating flow for a 150 Kg is 7.5 L/min and the maximum for a 40 kg patient is 20 L/min. Because pressure is related to flow squared, the pressure fluctuations are highly dependent on the absolute base flow rate plus oscillating flow rate or base flow rate minus the oscillating flow rate values

| | Flow type | | | |
|---|---|---|---|---|
| | Min gas flow ranges (L/min/kg) | Max gas flow range (L/min/kg) | Max flow for 40 kg px | Min flow for 150 kg px |
| Base: example 1 | 0.2 | 2.5 | 100 | 30 |
| Base: example 2 | 0.25 | 1.75 | 70 | 37.5 |
| Base: example 3 | 0.3 | 1.25 | 50 | 45 |
| Fluctuating: example 1 | 0.05 | 0.5 | 20 | 7.5 |
| Fluctuating: example 2 | 0.12 | 0.4 | 16 | 18 |
| Fluctuating: example 3 | 0.12 | 0.35 | 14 | 18 |

Figure 4:
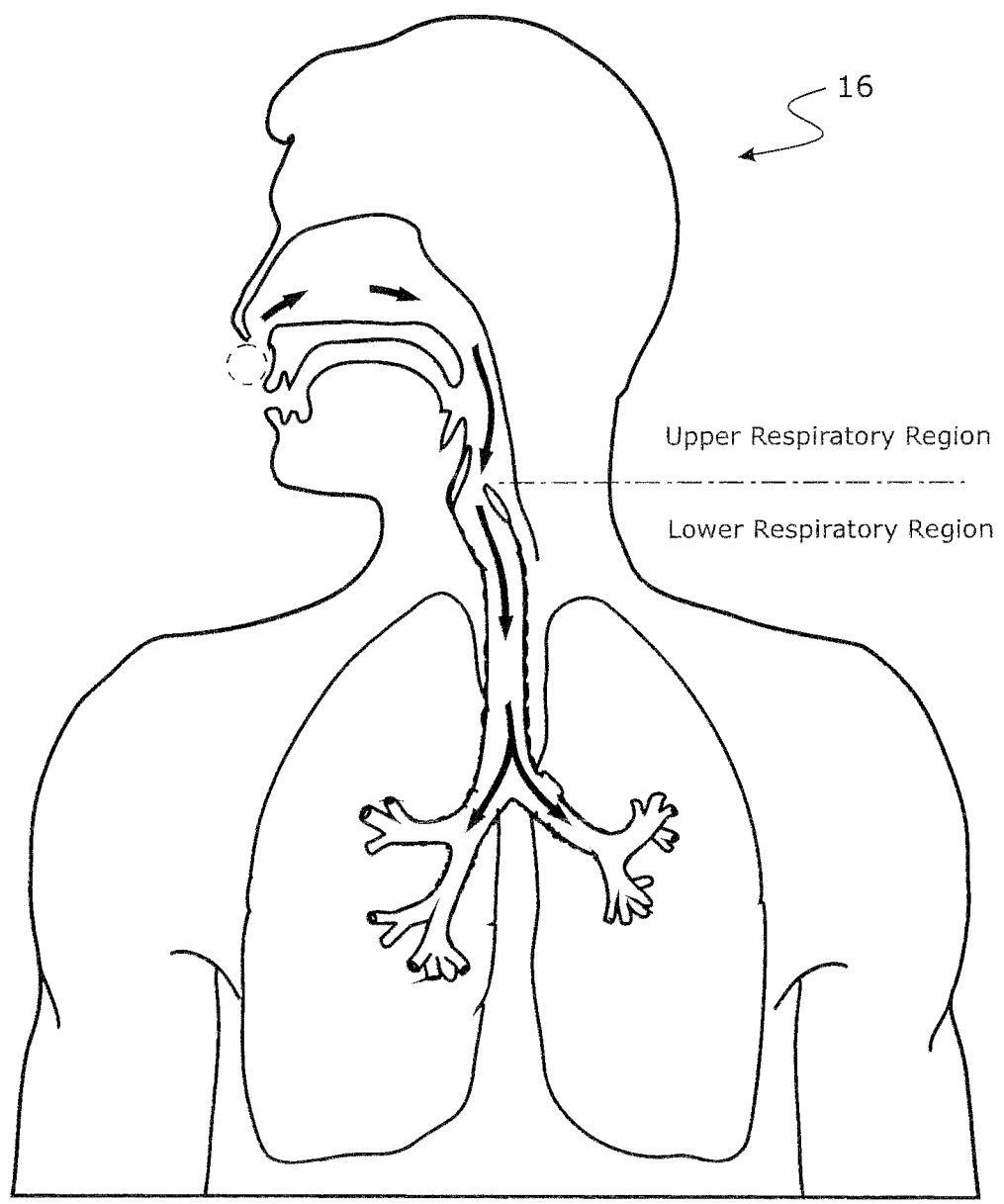
FIG. 4 illustrates airways of a patient.

Such relatively high flow rates of gases may assist in providing the supplied gases into a user's airway, or to different parts of a user's airway, for example such flow rates may allow for a delivery of such gases to the upper or lower airway regions, such as shown in FIG. 4. Upper airway region typically includes the nasal cavity, pharynx and larynx, while the lower airway region typically includes the trachea, primary bronchi and lungs.

Figure 10:
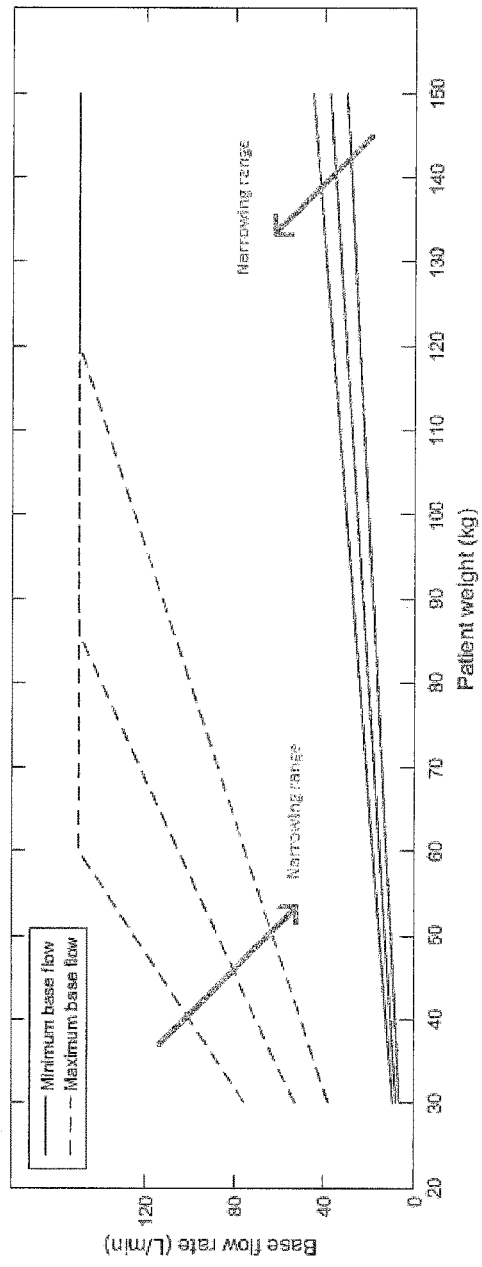
FIG. 10 illustrates possible flow rates delivered by apparatus and methods described.
Figure 10:
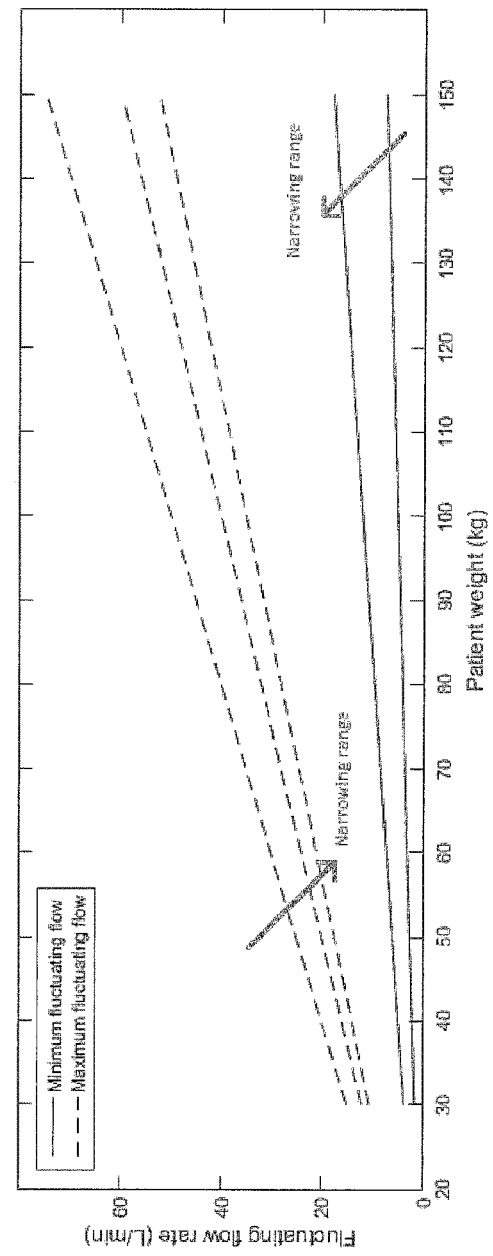

By way of non-limiting example, gas flow rates provided by apparatus and methods described herein could be as also in FIG. 10. All flow rates herein can be read as about or approximate, and strict compliance with them is not necessarily required.

When considering the various flow rates described above, it will be appreciated preferably there is not a negative flow rate (that would correspond to flow going from the patient up towards the apparatus). It is desired for flow to travel out from the apparatus to the patient. The maximum amplitude of an oscillatory component allowed is therefore equal to the baseline flow rate. If the amplitude became larger than this, the trough flow would be less than zero (i.e. this would correspond to flow being sucked by the apparatus up from the patient). As such, the flow rates above will be considered in this context and a particular flow rate parameter of a particular component might be influenced by the flow rate parameter of another component.

With a symmetric oscillating component, the maximum peak flow is by definition equal to twice the baseline flow. However, under certain circumstances an asymmetric oscillation could be applied to the flow rate whereby the peak flow could go higher than this, but the trough flow always remain at zero or above.

In more general terms, the controller 19 can be configured to control the flow source, generic modulator 59 and/or any other aspect of the apparatus to provide a varying gas flow with: the desired base flow rate and/or pressure (frequency and amplitude) and the desired oscillation component or components (frequency and amplitude) to improve oxygenation and $CO_2$ removal for the patient.

The controller can vary the base gas flow parameter(s) to create the oscillations using any suitable approach. For example, the controller might directly alter the pressure and/or flow rate by controlling the speed of the flow source. Alternatively, an external apparatus such as one or more gas flow modulators 59 might be used. The oscillations can be produced by any suitable mechanical and/or electrical configuration. Any suitable apparatus for oscillation can be used, such as valves (electrical, magnetic or pneumatic, for example), chopper wheels, transducers, pistons, or electronic modulation of the source, for example. FIG. 1 shows a generic modulator 59 operated by the controller for oscillating the gas flow, but this is by way of example and its position and nature should not be considered limiting.

The gas flow modulator(s) 59 (see FIG. 1) that creates the pressure oscillations may be positioned anywhere along the length of the system (from the patient end of the interface 15 to the flow source 12) and may achieve the oscillations 51/54 in a number of ways, such as some of the non-limiting methods and components listed below. The component 59 may be removable from the circuit and/or system.

Electronic valve such as proportional or solenoid valve
Rapid variations in blower speed, actioned by the controller.
Inline speaker or solenoid actuated diaphragm.
Inline linear actuator
A rotational or linear flow chopper
Any aerodynamic or mechanical flutter valve.
Bursts of compressed gas (i.e. air or oxygen) from a compressed gas source with control valve
Motor driving any arrangement of rotational to linear motion
Vibrating reeds that create oscillations
One way valve/flap that opens at certain pressures, optionally spring loaded The addition of flow/pressure oscillations to gas flow as described can do the following.

Reduce the time averaged flow rate/pressure necessary to achieve a certain level of oxygenation and $CO_2$ clearance. High flow rates can be perceived as less comfortable, so any ability to reduce the flow rate while maintaining the same oxygenation support is desirable.
Increase the total oxygenation and $CO_2$ clearance capacity of high flow gas delivery
Decrease the time required for pre-oxygenation The oscillation frequency (pressure or flow) of the gas flow could be anywhere from about 2 to about 200 Hz as previously described or otherwise as described elsewhere herein (more preferably, the frequency may be about 0.1 Hz to 3 Hz, or 0.3 Hz to 3 Hz) and have instantaneous pressure or flow amplitudes of up to 200 L/min and/or 50 cmH2O or otherwise as described elsewhere herein. The waveforms of the oscillations could be any suitable shape. Some examples of waveform shape are:

Sinusoidal
Square
Triangular
Saw tooth
Gaussian
Based on physiological waveforms (e.g. blood pressure or cardiogenic pulsations, cough, sneeze wave patterns etc.)

2.3 Determining Base and Oscillation Component Frequencies, Amplitudes and/or Phases for Varying Gas Flow In general terms the, the amplitude, frequency and/or phase of base and/or oscillation components (including the parameters thereof as stated above) are determined based on default parameters, user input, experimental data and/or physiological parameters. These can be set to optimise patient response. For example, the frequency and/or amplitude and/or phase of the base and/or oscillation components of a varying gas flow can be based on one or a combination of various considerations, such as (but not limited to) the following.

Sweeping the frequency and/or amplitude to find an optimum patient response.

The respiration rate and phase of the patient.

The resonant frequency of the lungs of the patient.

The resonant frequency of the chest cavity of the patient.

The heart rate (or more generally heart activity) of the patient.

The brain activity of the patient.

Random noise.

Clinician input, for example mean pulmonary artery pressure.

Experimental data or default/predetermined parameters.

Measurement of $O_2$.

Measurement of $CO_2$

Based on the above, the gas flow components have set instantaneous amplitude, frequency, phase, maximum and minimum amplitudes.

For example, oscillation components (that is the various parameters of components, such as phase, frequency and amplitude) could correspond to (be based on) or be synchronised/matched with one or a number of different respiratory or other patient parameters. "Correspond" more generally means to relate to or be influenced by, but not necessarily match (although it could comprise match also).

It has been determined that as $CO_2$ is exhaled through the trachea, a plug of $CO_2$ travels through the trachea and oscillating gas flow assist in clearing this plug from the airways. The apparatus and methods described above assist to provide $CO_2$ removal and/or oxygenation by providing for oscillating gas flow. The efficiency of $CO_2$ removal and/or oxygenation can be improved, where the parameters of the oscillation components are based on a physiological parameter, as described above. Oscillations could be chosen to have frequencies and/or phases that are matched to a physiological parameter frequency/phase, or some harmonic or other multiple of that frequency/phase. As another example, the oscillation components could be chosen to have an amplitude (instantaneous, maximum and/or minimum) that is proportional or inversely proportional to the amplitude of the physiological parameter (such as heart activity).

Some of these are described in more detail below, and various other examples described demonstrate how a gas flow component (oscillator or base component) can be based on a physiological parameter.

2.3.1 Heart Activity

Heart activity moves gas flow up and down the trachea of a patient. The heart has electrical signals that have a fundamental frequency. The electrical signals trigger the heart to pump, at that frequency, which in turn pumps blood with oscillatory pulses at that frequency. This influences oscillatory contraction and expansion of the lungs at that frequency, which in turn can move influence the oscillatory movement of gas up and down the trachea at that frequency. Heart activity can refer to any of these processes and the frequency of heart activity can refer to that frequency. While the oscillation at each stage above has the same frequency, each stage could have a different phase, due to a delay between each stage. For example, there could be a phase delay between the oscillating electrical signal occurring and the oscillating gas movement up and down the trachea.

During the delivery of nasal high flow to a patient, transport to the lungs occurs naturally by Aventilatory Mass Flow. However, the clearance of $CO_2$ from the lungs must occur against this net flow. Small oscillations of respiratory flow occurring at the same frequency as the heart activity have been observed during both inspiration and expiration. The inventors determined that cardiogenic pulsations combined with turbulence entrained from high pharyngeal flow cause longitudinal mixing of gas within the trachea. The mixing is sufficient to bring $CO_2$ up from the lungs, while also enhancing the transport of oxygen down the trachea. On the expiratory part of each cardiogenic cycle, a portion of the mixed gas in the trachea is then ejected into the strongly flushed pharyngeal region. For example, if a gas flow with an oscillating pressure is delivered with an amplitude of pressure fluctuations of 2 cmH2O, then approximately 140-200 ml of gas would be pumped in and then back out of the lungs over each pressure cycle. The airway dead space is approximately 150 ml, and so in this example about 0 ml-40 ml of gas would be cleared from the lungs each cycle. In this simplified case, clearance would begin to occur when the volume of gas pumped reaches 150 ml per stroke, and this would correspond to a pressure variation of 2.14 cmH20 (for the case of low lung compliance in the example)—1.5 cmH2O (for the case of high lung compliance) in this example. It is noted that the airway and lungs can readily withstand pressures of up to 5 cmH2O relative to atmospheric pressure.

As such, the inventors have determined that providing a varying gas flow with at least one oscillating component of the right frequency, phase and/or amplitude based on the heart activity frequency can assist the $CO_2$ clearance and/or oxygenation process. For example, if the oscillating component(s) has/have frequency(ies) the same as or near the cardiogenic pulsations (heart activity) creates this effect and facilitates $CO_2$ removal and/or oxygenation. The varying gas flow provided can be varied in synchronism with the heart activity, such as by varying the gas flow to have oscillation components with frequency(ies) matching those of the heart activity. The effect of this is to move gas up and down the trachea and contributing to $CO_2$ transport out of the lungs and oxygen transport in to them. This effect enhances the naturally occurring cardiogenically-induced oscillations of gas up and down the trachea. The net effect of the cardiac-synchronised flow variations to the flow is to greatly enhance the clearance of $CO_2$ achieved by cardiogenesis on its own (typically by a factor of between 3 and 10). More generally, the oscillation frequencies do not need to be synchronised with heart activity, but rather correspond to it in some way.

Figure 11:
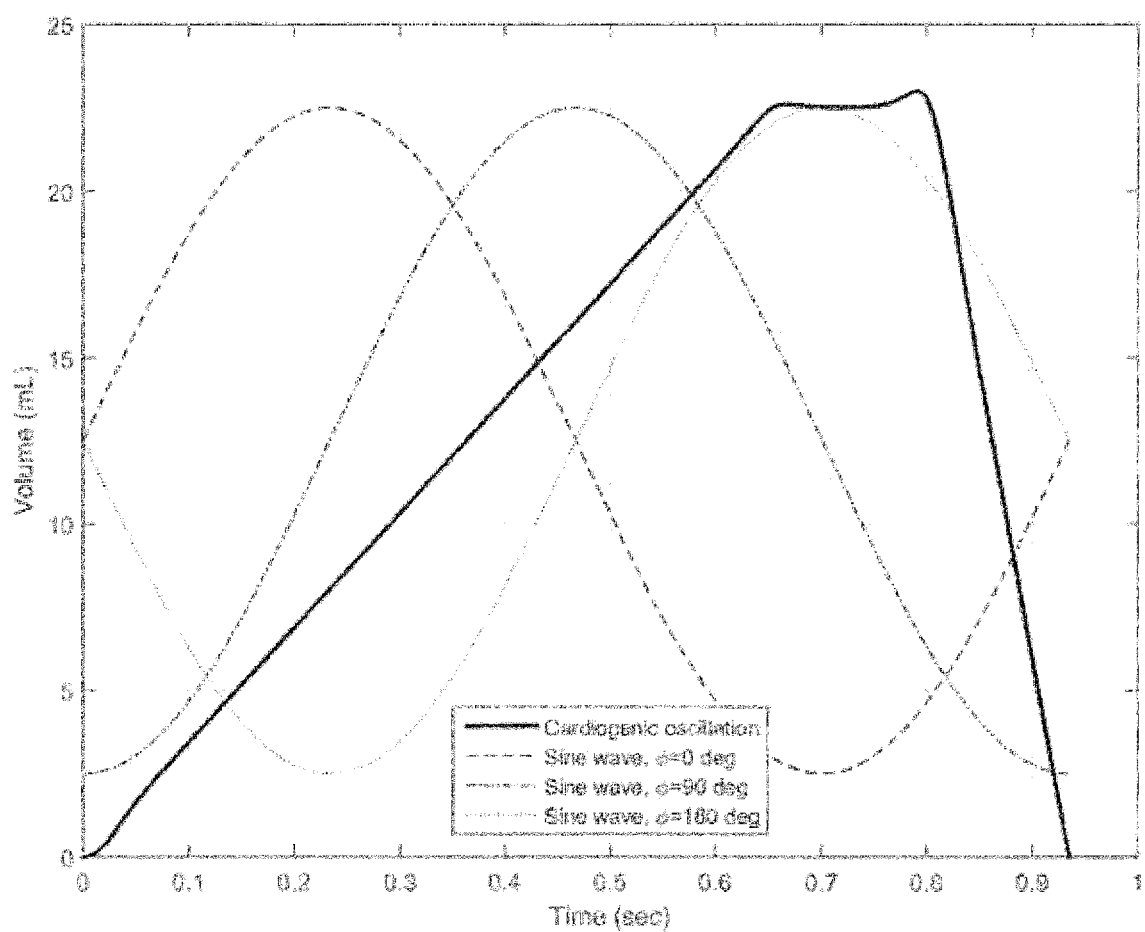
FIG. 11 shows a cardiogenic waveform for experimental example #1.
Figure 18:
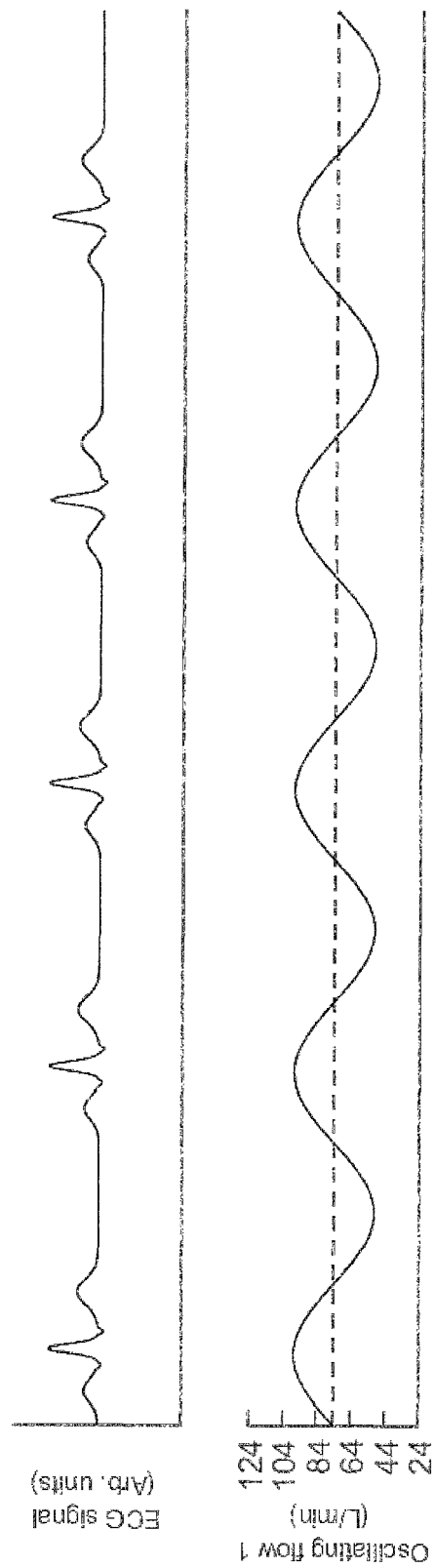
FIG. 18 shows an ECG signal, in relation to an oscillating gas flow.
Figure 19:
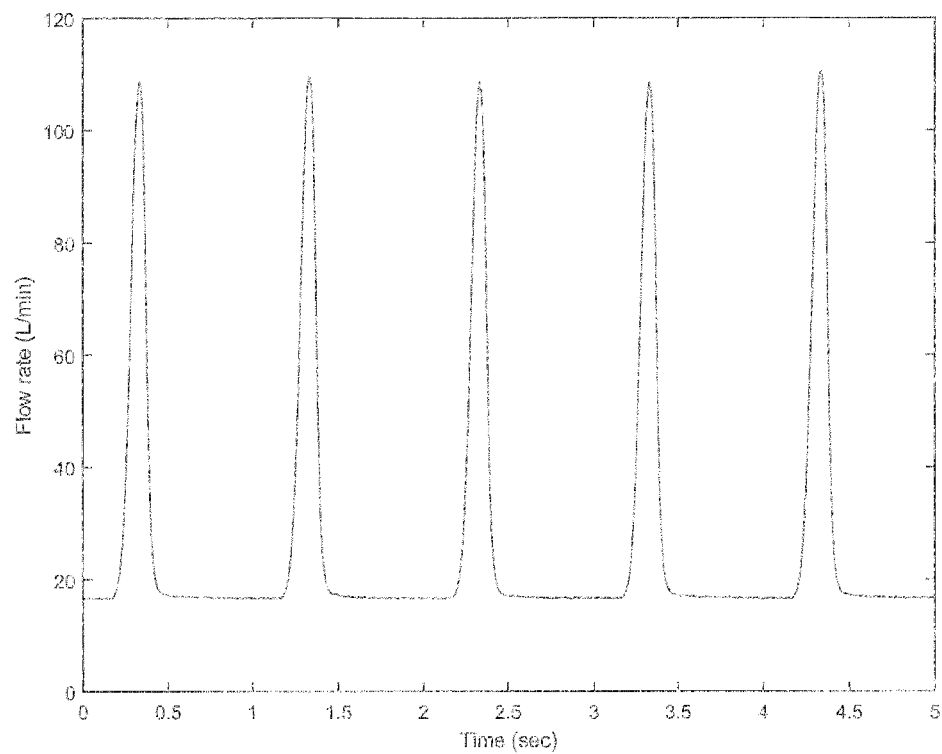
FIGS. 19 and 20 show alternative Gaussian oscillatory flow rate waveform and the related CO2 clearance.
Figure 20:
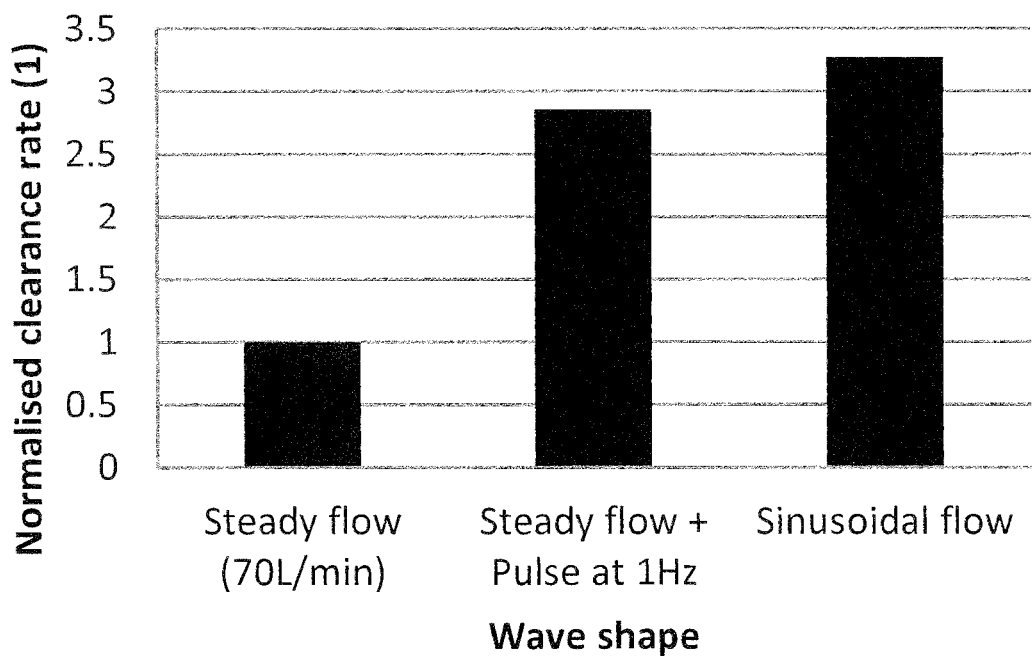

As one example of how a gas flow component can be based on a physiological parameter; heart activity can be sensed and the frequency of one or more oscillation components can be made to have a frequency the same as or similar to the heart activity. Additionally or alternatively, because there is a delay between the heartbeat and the gas flow in the trachea, each oscillation component might have a delay, such as a phase delay, relative to the heart activity waveform, to compensate for the gas flow delay. Preferably, the gas flow oscillation component is matched as closely as possible to the heart activity frequency (such as shown in FIG. 18 which shows an ECG signal showing heart activity and an oscillating component with the same or similar frequency), although some variance is possible, to provide optimum CO2 removal and/or oxygenation. The phase is preferably matched, although a phase difference still produces useful effects (such as shown in FIG. 11). Also, as mentioned earlier, a phase delay relative to one stage of heart activity, may help to align with the phase of another stage of the heart activity.

In one exemplary example, the controller 19 can monitor the patient's heart activity through a sensor (e.g. sensor 18$d$) and control the system 10 so that gas flow oscillations 52/55 are synchronised/matched or otherwise correspond with/are based on the patient's heart activity. The controller 19 can be configured to control the flow source 12 to provide a gas flow that oscillates 52/55 at the same frequency as that of the (or otherwise based on) patient's heart activity frequency to increase the mixing of the gases, promoting oxygenation and CO2 clearance. The oscillation could be in phase, in antiphase (or constant relative phase) or out of phase with the heart rate but preferably in or close to in phase (or with a phase delay) as previously described. In a preferred example, the frequency of an oscillating component can be about about 0.1 Hz to about 3 Hz, or preferably 0.5 Hz to about 3 Hz, and, which corresponds to the frequency of typical heart activity.

In one example, the patient's heart activity (including "heart beat" or "heart rate" or any of the heart activity stages as mentioned earlier) could be monitored using sensor 18$d$ and the output signal could be used as the input into the controller to determine the frequency of gas flow oscillation 52/55. For example, the heart activity could be monitored using sensors e.g. 18$d$ in one or more of a number of ways. Non limiting examples follow.

Using a heart rate monitor (heart activity sensor). Flow sensor to measure gas flow in the trachea.

Using the plesythmograph signal from a pulse oximeter probe.

Using an ECG signal picked up by electrodes (sensors) attached to the skin (usually the chest) and coupled to a very sensitive amplifier.

In each case, it is the output electrical signal which fluctuates in synchronism with the heart activity that is connected to the controller.

Alternatively or, the user could be prompted to enter the heart activity information into the I/O interface 20, from empirical data, previously recorded heart activity, or some other source. In this case, the controller 19 receives input relating to heart activity of the patient from the I/O—such as from a clinican who takes the patient's pulse. Alternatively or additionally, the heart activity information could be in a memory forming part of or separate to the controller. In this case, the controller 19 receives input relating to heart activity of the patient from the memory, which could be stored based on e.g. empirical data of typical heart activity frequencies and/or typical gas flow oscillation frequencies that prove effective. For example, resting heart rates are typically between 40-100 bpm (0.67-1.67 Hz) but could be in the range of 30-180 bpm (0.5-3 Hz) under extreme physiology (e.g.

under medical procedures or intense exercise).

Alternatively, the gas flow system 10 could comprise an electrocardiogram or heart rate monitor or echocardiograph (which could be considered heart activity sensors in the system). In this case, the controller 19 receives input relating to heart activity of the patient from the sensors in the system.

Irrespective of how the heart activity is measured or otherwise determined, it can be used by the controller to determine a suitable frequency(ies) for the oscillation component(s) of the varying gas flow. For example, if the heart rate was measured at 80 beats per minute the high flow system could be set to oscillate 52 the flow between 70 L/min and 40 L/min 80 times a minute (1.333 Hz).

In more general terms, the varying gas flow oscillation component frequency and phase is based on the gas flow in the trachea. Heart activity frequency can be used to determine the frequency of gas flow in the trachea as described above, and therefore the gas flow oscillation component frequency and phase is based on the heart activity frequency. However, another measure could be used for trachea gas flow. For example a flow sensor could be placed to measure flow rate in the trachea, and the oscillation component frequency and phase based on the gas flow frequency is determined from the flow sensor.

Where a sensor is used, there can be continual or periodic feedback of the heart rate activity so the frequency and/or of the oscillating component can be adjusted when it drifts from the desired frequency or phase.

The human body is very adaptable and it is possible the heart would synchronise with oscillatory flow 52/55. Therefore, in an alternative, it is possible the user could enter an oscillatory frequency 51/54 they wished the gas flow to be at and encourage a change in the frequency of the heart. In this case, the user could choose to only have the set frequency or choose to provide some variation to the frequency (e.g. if the user set 80 beats per minute the high flow system could cycle between ±4 beats per minute around the set point). Variation is thought to be beneficial.

The controller 19 can controller the flow source 12 to produce gas flow oscillations in accordance with one of the following.

The oscillations 51/54 are synchronised so that as the heart expands, an increase in gas flow is delivered, flushing the CO2 from the airway and displacing it with oxygen from the flow source. As gas moves up the trachea as a result of the cardiogenic oscillation the gas flow is reduced to facilitate it coming up. As the gas goes down the trachea as a result of the cardiogenic oscillation the gas flow is increased.

The oscillations 51/54 are synchronised so that as the heart expands, a decrease in gas flow is delivered (this could be positive, zero, or negative), causing a suction effect on the CO2 drawing it out from the airway and allowing oxygen to replace it when the flow is increased again.

It will be appreciated that in addition to determining one or more oscillation/base components for a varying gas flow based on heart activity, one or more other oscillation/base components of that varying gas flow could be determined based on other physiological parameters (such as those described next). Any reference throughout the specification to a varying gas flow with one or more oscillation/base components based on heart activity does not preclude that varying gas flow having one or more other oscillation/base components based on some other parameter, such as a physiological parameter. Multiple oscillatory components, each with frequency, phases and/or amplitudes all determined based on multiple different physiological or other parameters could be determined and combined to form a varying gas flow for CO2 removal and/or oxygenation. For example, this could be an oscillating gas flow has a plurality of oscillating gas flow components at a plurality of frequencies. All the examples described herein could be used alone or in combination.

2.3.2 Respiratory Rate

In one example, to assist with determining a suitable oscillation waveform for the gas flow, the controller can monitor the respiratory (breath) flow of the patient (using one or more of the sensors) to determine parameters and/or phases of the respiratory flow and the patient's requirements. For example, the controller 19 can utilise parameters of the respiratory flow wave (including the phase of breath and/or the transition between inspiration and expiration). Methods and apparatus for respiratory flow wave, meeting (e.g. peak) inspiratory demand and estimating (e.g. peak) inspiratory demand could be used. It should also be noted that the following can utilise switching modes of operation between inspiration and expiration. The exact moment of switching should not be limited to the exact transition point.

By determining the patient's respiratory flow the controller 19 could be configured to operate the flow source 12 and other aspects of the system 10 to do one or more of the following.

Superimpose oscillatory flow 51 (such as in FIG. 5F) on the respiratory flow.
Determine the phase of the breath (inspiratory, expiratory), and
  only deliver oscillatory flow during a set phase (inspiratory or expiratory or near the end of expiration),
  Stop flow during expiration to allow the lung to passively expire; the "stop" flow being for example 0 L/min or a low flow (e.g. below 20 L/min), and/or
  provide oscillatory flow 52 (such as in FIG. 5F) and intermittently provide negative flow for the expiratory portion of a breath; the "negative" flow being for example 0 L/min or a negative flow that sucks flow from the patient.

Oscillatory flow could be delivered through the patient interface (e.g. nasal cannula or nasal mask) 15 as done in traditional high flow therapy. However, in present embodiments where oscillating gas flow 52/55 is provided during medical procedures (such as anaesthesia) there are other possible delivery configurations also, which comprise the following.

A device (e.g. mask and cannula combination interface 15) could be used to deliver oscillatory flow 52/55 through the nose and mouth. The delivered oscillations could be the same or different for the nose and mouth. They could also be delivered at different times (e.g. only through the nose, then only through the mouth)
A device (e.g. extended Endotrachael tube) could be used to deliver different oscillatory flows 52/55 into the left and right bronchi to maximise the potential to meet the resonant frequency of each side of the lungs.

2.3.3 Resonant Frequency Lungs

In another example, the controller can control the system so that gas flow oscillations are synchronised/matched or otherwise correspond with the patient's lung resonant frequency or frequencies. Delivering a frequency that matches the resonant frequency/ies of the lungs as a whole, or a spectrum of frequencies that encompasses the resonant frequency of the various airways of the lungs encourages mixing, oxygenation and CO2 clearance. The resonant frequency/ies will be different for each patient. The controller 19 is configured via the sensors (e.g. 18*d*) and/or other inputs to detect the resonant frequency of the lungs. This could involve operating the flow source provide oscillating gas flow 52/55 with a sweep of different frequencies over a range of frequencies while a patient is breathing, and monitoring via the sensor(s) respiratory parameters to provide feedback on when oxygenation and/or CO2 clearance is greatest. Possible respiratory parameters can comprise any one or more of the following.

CO2 (expired, transcutaneous)
O2 (expired, transcutaneous, SpO2)
Respiratory rate (lower CO2 concentrations lead to reduced respiratory rates)

Continuous monitoring of the respiratory parameters by the controller 19 could be used to ensure the frequency is matched throughout the anaesthetic or other medical procedure period.

In another example, the controller 19 is configured to modulate the gas flow 13 with noise to produce gas flow oscillations 52/55 to vibrate the airways at different frequencies. Instead of using a patient specific frequency, such as a resonant frequency, a random signal of random frequencies (noise) could be used by the controller to produce a noisy oscillating gas flow to encompass the majority of the population's optimal resonant frequencies.

2.3.4 Resonant Frequency Chest

In another example, the controller 19 can control the system 10 so that gas flow oscillations 51/54 are synchronised/matched or otherwise correspond with the resonant frequency of the chest wall of the patient. Respiratory inductance plethysmography (RIP) is a method of evaluating pulmonary ventilation by measuring the movement of the chest and abdominal wall. The controller 11 can receive input from a chest band or other device/sensor 18*d* to measure the chest wall movement. The controller 19 then controls the flow source 12 to deliver an oscillating gas flow 52/55 at a frequency that causes the most movement in the chest and abdominal wall to encourage gas movement and mixing, promoting oxygenation and/or CO2 clearance. The controller 19 might sweep the flow source 12 oscillations through a range of frequencies to ascertain the (resonant) frequency that optimises chest and abdominal wall movement.

2.3.5 Diaphragm Contraction

In another embodiment, the controller 19 can control the system 10 so that gas flow oscillations 52/55 are synchronised/matched or otherwise correspond with the frequency of the diaphragm muscle contraction. Electromyography (EMG) is a technique that evaluates and records the electrical activity of muscles. The controller can receive input from an EMG system, which is used by the controller 19 to determine the frequency of oscillation. The controller 19 then operates the flow source 12 to provide a gas flow that oscillates 52/55 at the same frequency as diaphragm muscle contraction to increase the mixing of the gases; promoting oxygenation and CO2 clearance.

2.3.6 Brain Activity

In another embodiment, the controller 19 can control the system 10 so that gas flow oscillations 52/55 are synchronised/matched or otherwise correspond with the frequency of brain electrical activity. The controller 19 can receive input from an EEG system or other sensor 18*d*, which is used by the controller 19 to determine the frequency of oscillation of neuron firing. The controller 19 then operates the flow source 12 to provide a gas flow that oscillates 52/55 at the same frequency as neuron firing which may increase the mixing of the gases, promoting oxygenation and CO2 clearance.

2.3.7 Additional Considerations

Sensing CO2 in the patient and providing that to the controller enables further automatic adjustment of the gas flow components to optimise the condition of the patient.

Sensing the oxygen saturation level and providing that to the controller enables automatic adjustment of the gas flow components to optimise the condition of the patient. The flow rate can be increased or decreased as oxygen saturation respectively decreases or increases In another example, sensing the partial pressure of oxygen in the blood is used to control the apparatus. The partial pressure of oxygen in the blood provides an indication of the amount of oxygen stored in the body. If this starts to fall—for example due to progressive atelactesis, then measures should be taken to increase it. It is therefore advantageous to monitor the partial pressure of oxygen in the blood with time, to determine if it is falling (saturation measurements alone will not allow this to be done accurately at high partial pressure levels). If the partial pressure of oxygen in the blood starts to fall, the machine, or clinician, can take action to prevent further fall before the blood oxygen saturation level starts to fall and the patient is compromised.

At the same time, the controller changes the characteristics of the waveform so that the time for which the lower flow rate is applied during the cycle is decreased, and consequently, the time for which the higher flow rate is applied is increased. In the case of oscillating flow rates, when the flow rate oscillates towards the minimum flow rate, the time it remains at or near the minimum may be reduced compared with the time it remains at or near the maximum flow rate. This can be achieved through summation of various oscillating components, through controlling a duty cycle ratio of the waveform, providing a square wave component with an appropriate ratio, or via other suitable means. This increases the mean flow rate. The airway and lungs are held at higher pressure while the flow rate is at or near the maximum flow rate, therefore applying this characteristic to the waveform increases the time for which the airway and lungs are held at a higher pressure—thereby increasing the mean pressure, and further reinflating the lungs. This is an example of the controller changing the waveform applied.

The controller continues to monitor the blood oxygen partial pressure level. If the levels falls further, the controller increases the upper (maximum) and lower (minimum) flow rates again and also changes the fractions of the cycle for which the upper and lower flow rates are applied as described above to further increase the airway mean pressure.

The gas flow can have an oxygen fraction of 100%, or 30-40% or 40-50% or 60-70% or 80-90% or 90-100%. The gas flow can have an oxygen fraction of at least about 21% and comprises one or more of nitrous oxide, nitric oxide and/or helium.

At any time during the monitoring and control process described above, the clinician may interrupt the monitoring and control cycle, and manually set the value of upper (maximum) and lower flow (minimum) rates, and the period (frequency) of the flow variation cycle to values which in their judgement may provide better outcomes for the patient. Following manual setting of these parameter, the clinician then has the option of re-engaging the automatic monitoring and control process, or retaining the manually set values.

The gas flow can have a flow rate, wherein a first flow rate provided prior to the medical procedure and a second flow rate is provided during the medical procedure, and optionally a third flow rate after the medical procedure. The second flow rate can be greater than the first flow rate; and/or the third flow rate is less than the second flow rate. The first flow rate is about 15 L/min to about 90 L/min, or about 20 L/min to about 80 L/min, or about 25 L/min to about 60 L/min, or about 30 L/min to about 50 L/min, or about 40 L/min, or about 30 L/min; and/or second flow rate is about 20 L/min to about 150 L/min, or about 40 L/min to about 120 L/min, or about 50 L/min to about 100 L/min, or about 60 L/min to about 80 L/min, or about 70 L/min, or about 60 L/min; and/or the third flow rate is less than about 90 L/min, or less than about 70 L/min, or less than about 50 L/min, or less than about 40 L/min, or less than about 20 L/min, or about 40 L/min, or about 30 L/min.

In another example, exhaled CO2 is used as input for control of the apparatus. Exhaled CO2 information can be used as follows.

1. If the patient is breathing, the partial pressure of CO2 in the mouth will rise substantially on the expiratory part of the breathing cycle. This is detected by the controller which is then able to automatically determine if apnoea has commenced, and adjust the flow parameters accordingly. This might—for example—consist of switching the flow from an initial constant flow rate of 30 l/min to a flow pattern which varies cyclically in synchronism with the heart activity from a lower flow rate of 30 l/min to an upper flow rate of 70 l/min and then back again.

2.4 Examples of Using Varying Gas Flow for CO2 Removal and/or Oxygenation

Figure 6:
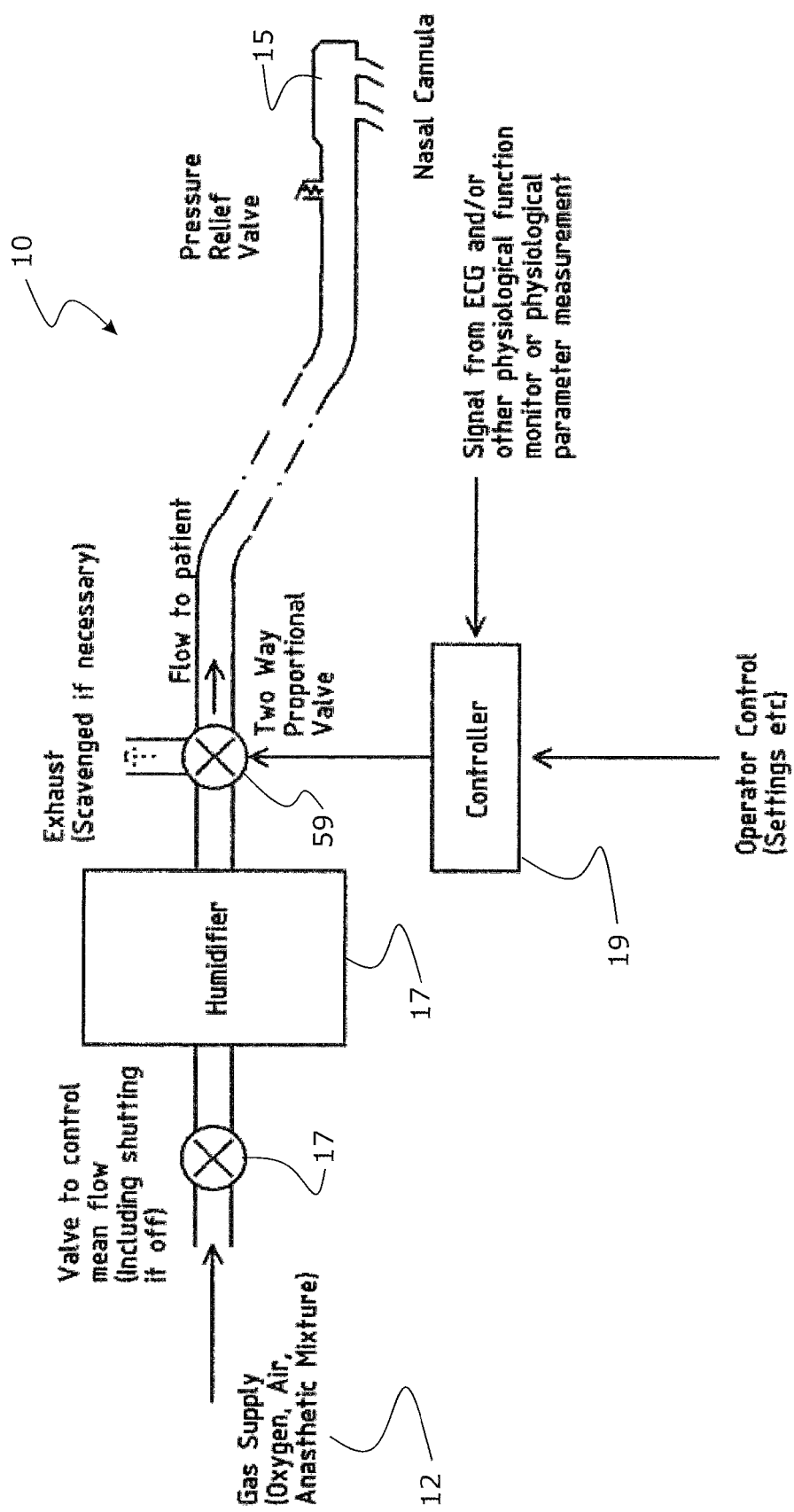
FIGS. 6 and 7 illustrate an apparatus/system for oxygenating a patient with high flow gas in relation to anaesthesia and the resulting parameter waveforms according to one example.

One exemplary and non-limiting example of an apparatus and method for supplying a high flow of humidified gas for oxygenation and/or CO2 removal, will be described with reference to FIG. 6 where the flow rate is cycled periodically to vary the pressure applied to the trachea and cause ventilation of the lungs. The apparatus is one example of the generic embodiment in FIG. 1. In this embodiment, the modulating device is a valve 60 after the humidifier.

In this setup dry gas, which may be air, oxygen, or any mixture of gases appropriate for the therapy to be applied to the patient is supplied from a flow source 12 to a humidifier 17 via a valve 59 which enables control of the mean flow rate. A pressure regulator can also be incorporated into the gas supply. Mean flow rate and oscillating flow rate could be provided on two separately controlled lines, in an alternative.

The humidifier 17 humidifies the gas to a level appropriate for the therapy to be used—normally this would be to just below saturation level at 37 degrees C., but may be any level appropriate for the patient. The humidified gas 13 passes through a two way proportional valve 60, which is controlled by a controller 19. The proportional valve may divert gas to the patient, or to an exhaust—or to any combination thereof. The purpose of using a two way valve is to assist that flow through the humidifier is as constant as possible (thereby providing optimum humidification), notwithstanding that flow to the patient may vary over a wide range under the control of the controller.

The controller 19 controls the valve 60 to vary the flow rate going to the patient cyclically to achieve a varying gas flow with the desired oscillation parameters as previously described, leading to the desired ventilation described above. The controller 19 is provided with input signals from measurements of patient physiological functions for example:—heart activity, spontaneous breathing etc. and physiological parameters for example:—levels of oxygenation, the partial pressure of CO2 in the blood etc. It is able to synchronise the flow fluctuations with periodic physiological functions so that the fluctuating flow can—for example—operate to enhance the effect of cardiogenesis for apnoeic patients or enhance spontaneous ventilation for breathing patients, where this is considered appropriate by the clinicians. Note, however, that in many applications—particularly for apnoeic patients—breath synchronisation will not be necessary.

Parameters such as upper and lower flow rates, the period of the flow rate cycle, and the waveform of flow versus time during the flow rate cycle may be set by the controller from inputs provided either by a human operator, or automatically from measurements of patient physiological functions and patient physiological parameters.

Figure 7:
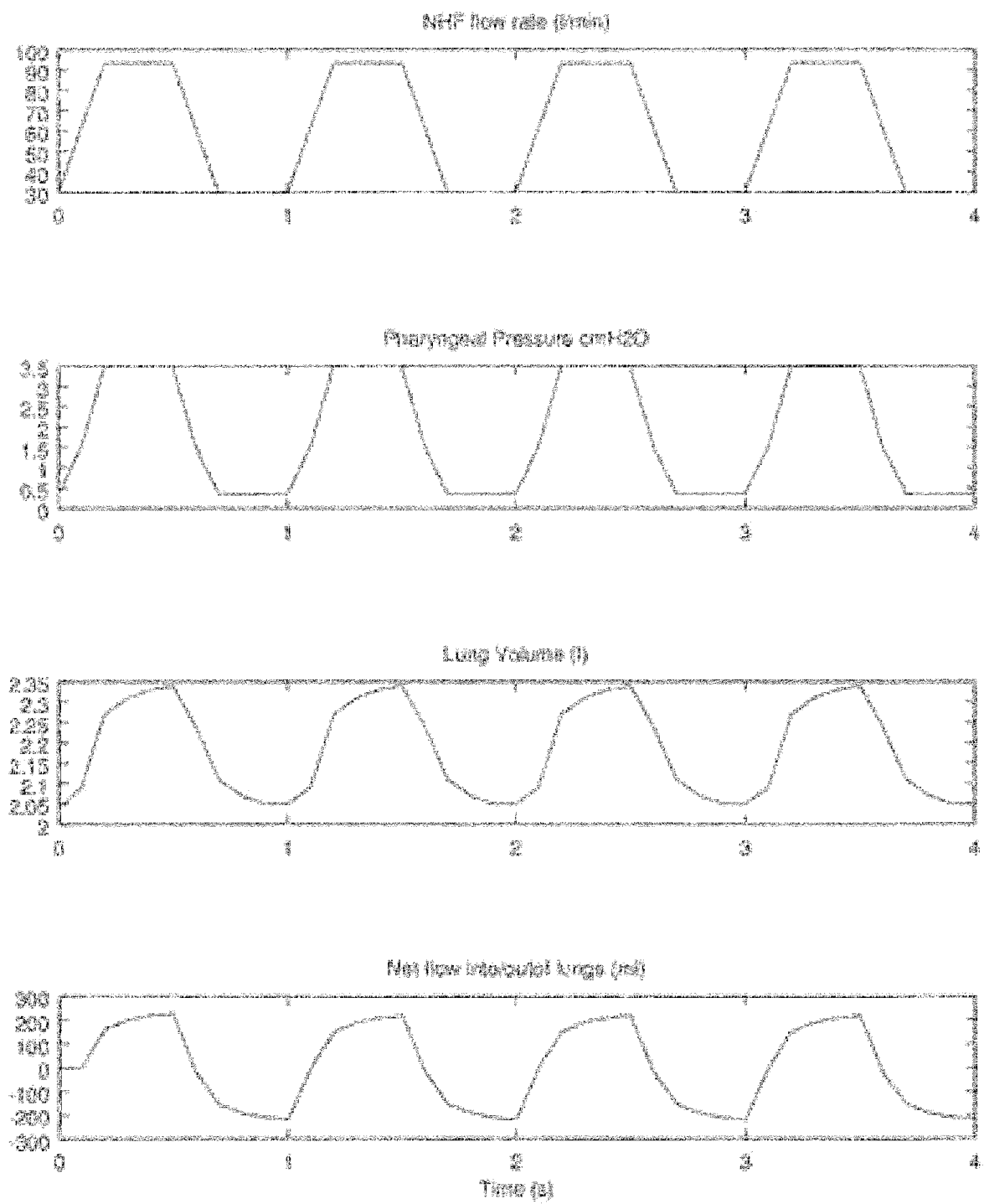

FIG. 7 shows the relationship between the delivered/applied flow rate, pharyngeal pressure, lung volume, and net flow of gas into and out of the lungs after dead space has been accounted for—for an apnoeic patient with open mouth and typical airway dimensions.

In this example, the period of the flow rate cycle was 1 second and flow rate cycles were started at t=0. If a normal patient were ventilated in this way, the minute volume achieved would be approximately 13 l—well above the minimum necessary.

Figure 8:
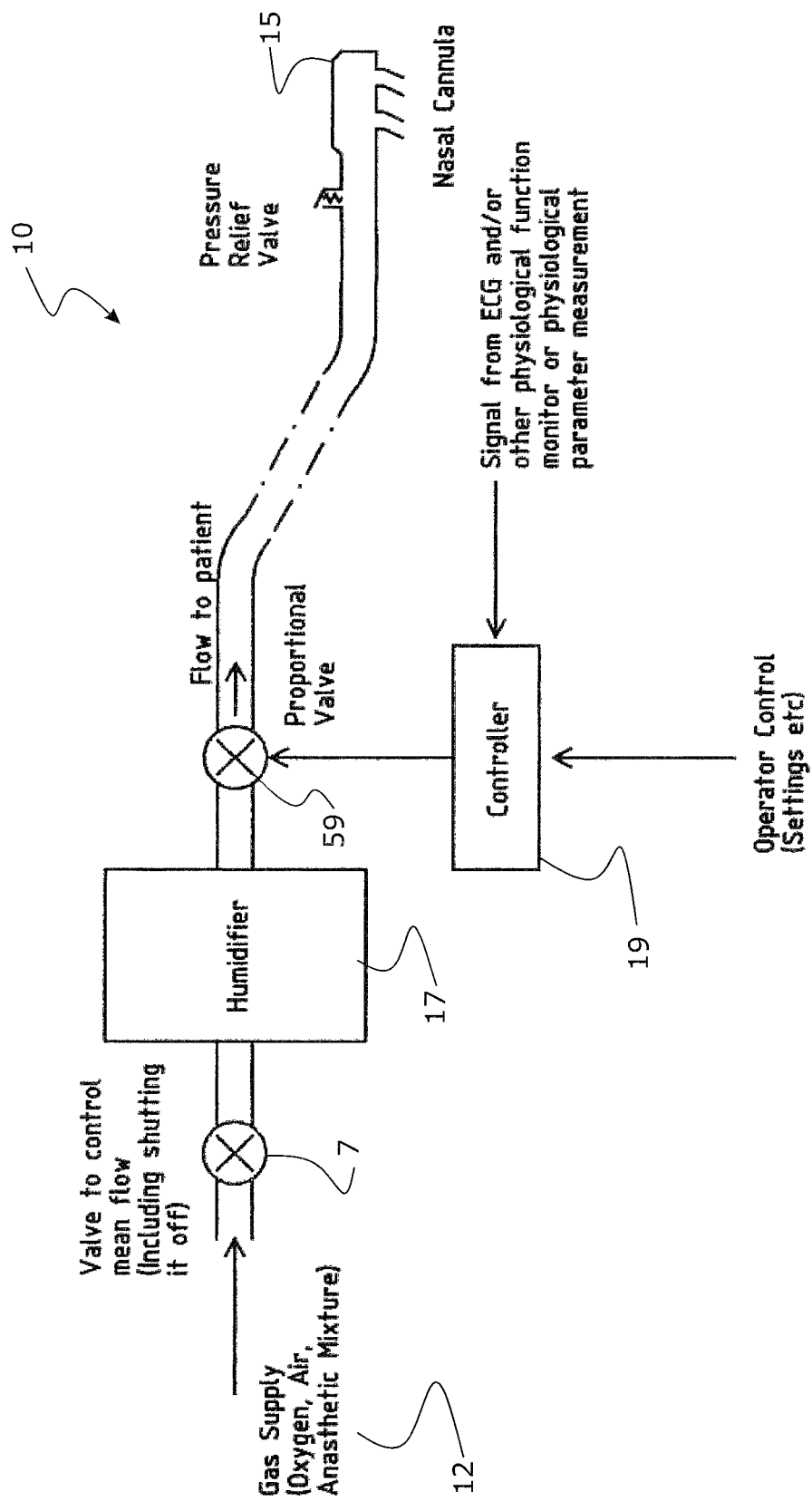
FIGS. 8 and 9 illustrate an apparatus/system for oxygenating a patient with high flow gas in relation to anaesthesia according to alternative examples.

FIG. 8 shows another example embodiment (this time a simplified arrangement) for use where the humidifier and circuit is able to respond to rapid fluctuations in flow. Here, the valve used to control the flow is a proportional valve which turns the overall flow in the system up and down.

Figure 9:
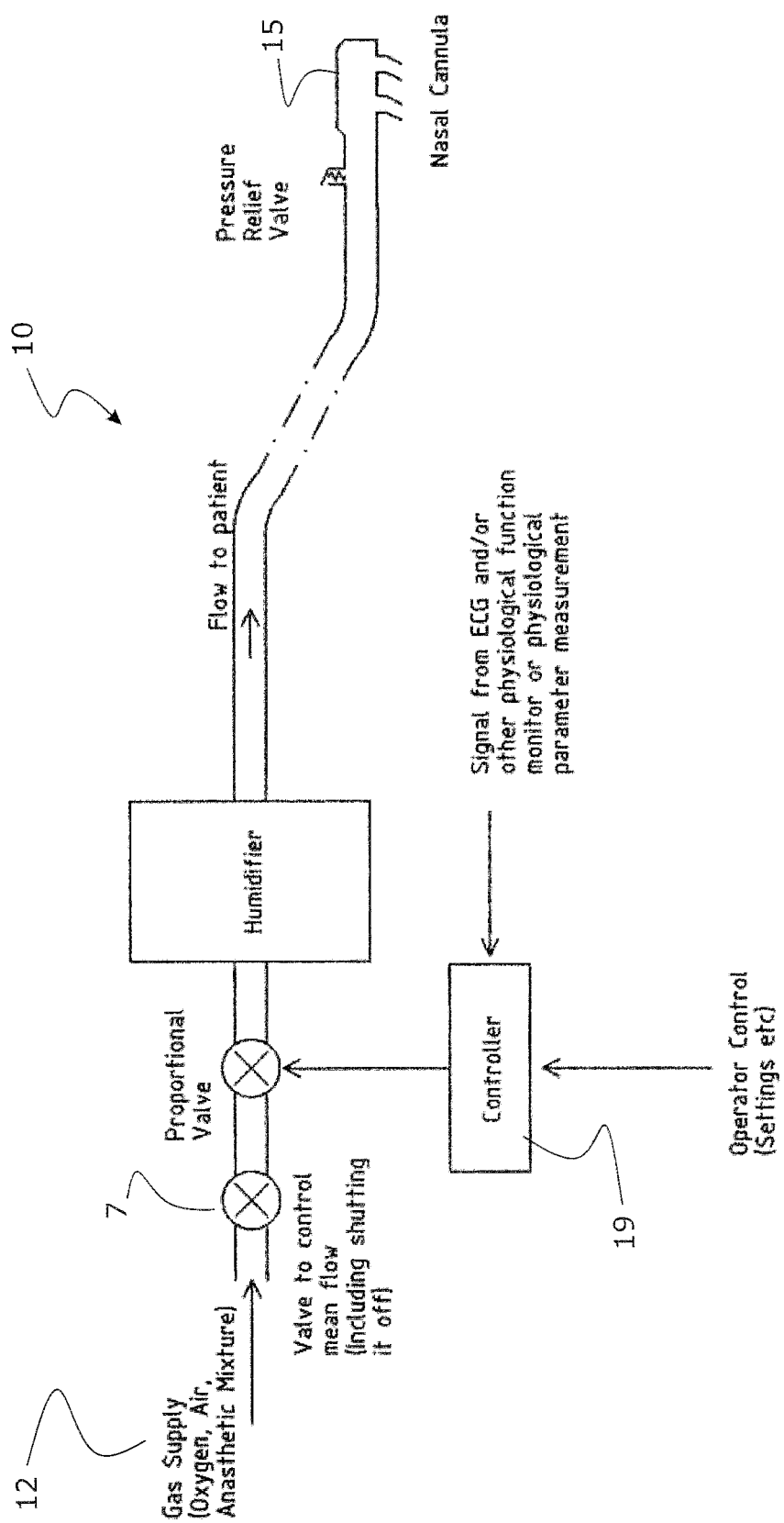

Finally, FIG. 9 shows another example embodiment where the flow control valve is placed in the gas supply to the humidifier. This has advantages because the proportional valve is able to work in dry gas—rather gas which is close to saturation point in humidity—and design of reliable mechanisms which provide rapid and precise control is easier if the gas is dry.

In these example embodiments, an optional pressure relief valve can be provided close to the cannula in order to prevent barotrauma to the patient in the event that the cannula seals into the nose and the mouth is closed. The pressure relief valve could be replaced by a pressure measurement system which is connected to the proportional valve controller, so that the controlled turns the flow off if the pressure at the patient rises above a certain level.

As noted earlier, the present inventors have determined that by oscillating the flow (as described herein) in the trachea in a patient who is not breathing spontaneously gas is driven down the trachea to the lungs, and then back up from the lungs to the trachea—that is, it provides a mechanism for transporting gas in and out of the lungs.

2.5 Experimental Results Demonstrating Benefits of Varying Gas Flow

The following experimental discussion demonstrates this.

2.5.1 Experimental Apparatus

A benchtop experimental model was used to investigate the effects of oscillating high nasal flow (HNF) on gas exchange and carbon dioxide (CO2) clearance during apnoea. The model is a suitable representation of the embodiments of the apparatus 10 described herein and is shown in FIGS. 12A, 12B.

The model consisted of an adult upper airway geometry connected to a lung reservoir with compliance similar to that of the lung-chest wall system in real physiology (approximately 45 ml/cmH2O). It included the nasal and pharyngeal cavity, an open mouth, trachea, and primary and secondary bifurcations up to the sixth generation. The lung reservoir was plumbed with various controllers and sensors to introduce/monitor percent concentration of CO2 in the lung, measure the incoming flows, and monitor the static lung pressure.

In addition, a cardiogenic pump was used to simulate the effects of the heart on gas motion in the airways. It is thought that the pulsatile nature of blood flow (caused by effects of the heart) causes miniscule squeezing of the lower airways which in turn drives a plug of gas in the upper airways and trachea. The pump consisted of a numerically controlled stepper motor-syringe system and oscillated a known volume of gas at a specific wave shape and frequency into the lung reservoir. Cardiogenic oscillations can be approximated with a trapezoidal waveform of with amplitudes (stroke volume) of 5-30 mL and frequency of 0.5-3 Hz. The cardiogenic parameters (waveform, frequency, and stroke volume) will vary between patients and within the same patient at different times due to the variability in heart rate and blood pressure. FIG. 11 shows an example of a piecewise linearly approximated cardiogenic waveform with parameters derived from one experimental realisation. The fit was based on a heart rate of 64.2 bpm, stroke volume of 22.5 mL, and rise and delay fractions of 0.7 and 0.15 respectively. FIG. 11 also includes plots of shifted sinusoidal waves which illustrate (but not to scale) the phase shifting in the varying high gas flow and that will be discussed in example 3 (note that positive values imply gas pushing into the lungs).

Figure 12A:
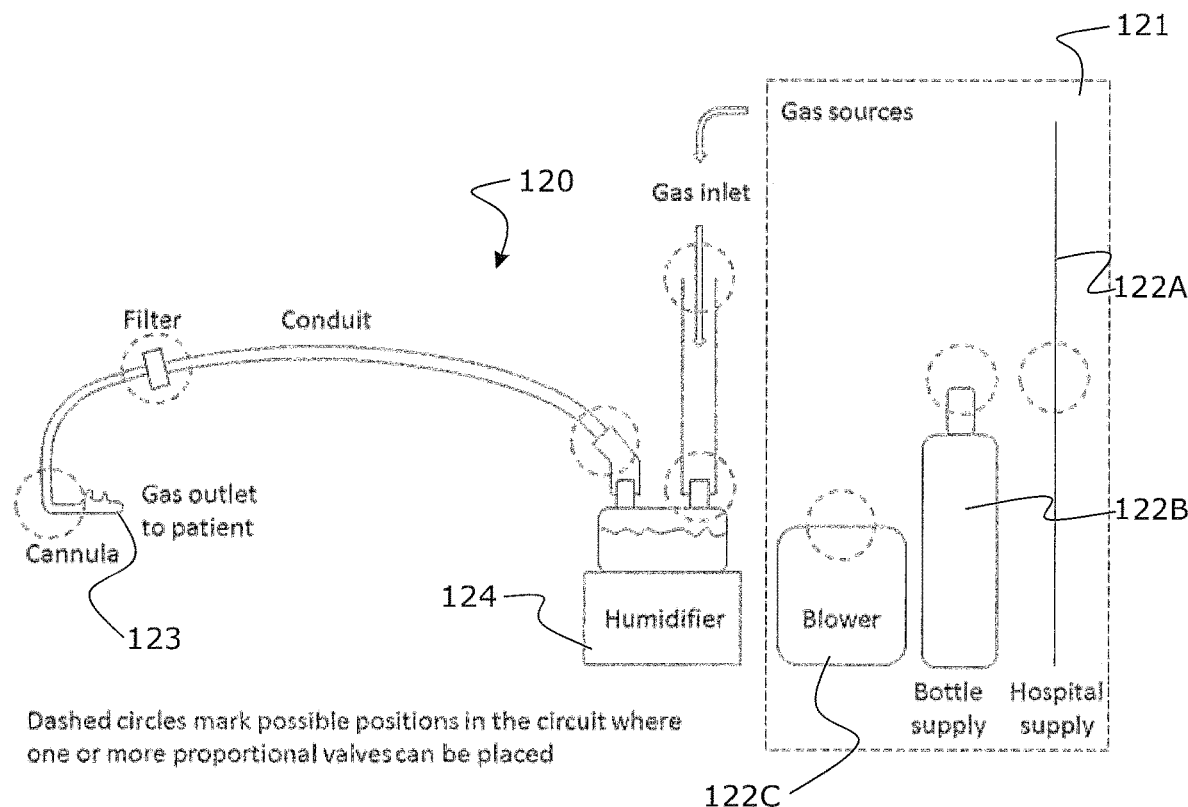
FIGS. 12A and 12B show an experimental apparatus.
Figure 12B:
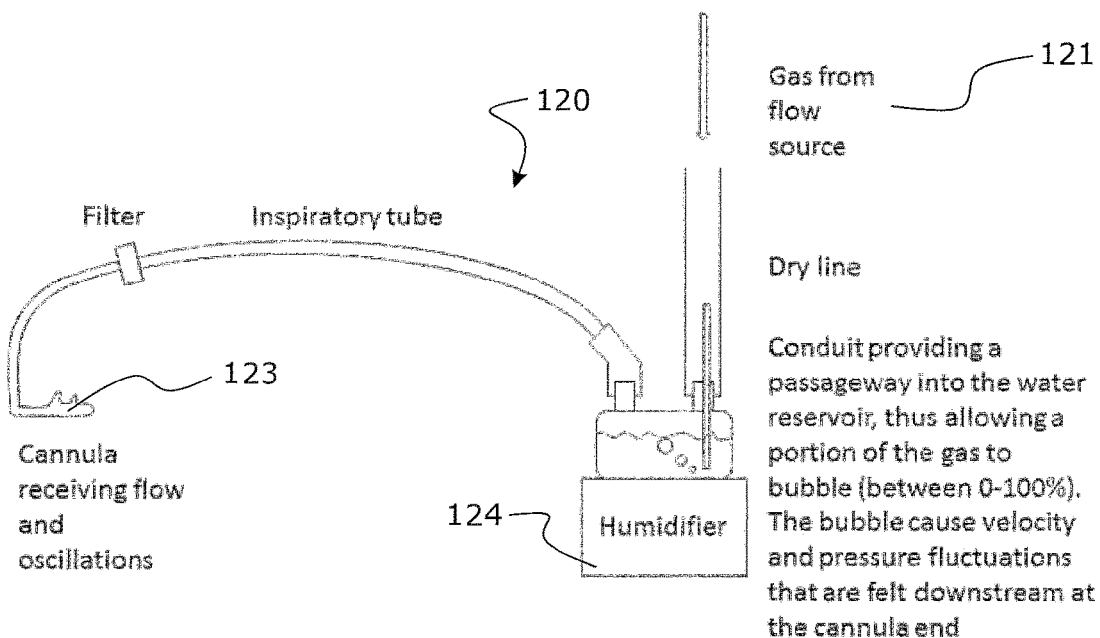

Referring to the experimental apparatus 120 in FIG. 12A (which is a suitable model for the apparatus 10 of embodiments described herein), gas flow oscillations were delivered using a flow source 121 from a wall supply 122A, bottle supply 122B and/or blower 122C) to the nasal cavity using a high flow nasal cannula which was connected in series to a regulator and a proportional valve. The latter is an electronically controlled orifice-type valve with sufficient resolution to produce arbitrary waveforms composed of multiple frequencies. In clinical practise one or more valves could be positioned near the gas source (wall, bottle, or blower) with or without a regulator/pressure relief in series; prior or post the humidifier 124 and/or the control system; and prior or post the end of the delivery circuit but before the cannula 123 (see FIG. 12A). There are certain advantages of placing the valve in such locations. For example, valves near the gas source or inlet could shut-off or divert the flow in case of medical emergencies or when excess pressures are sensed at the patient end. Placing the valves near the humidifier/controller simplifies device integration with the rest of the system. Placing the valve in close proximity to the cannula minimises the dissipations of high frequency flow oscillations in the patient's circuit due to the compliant nature of respiratory conduits.

The method for flow oscillations is not limited to electronic proportional valves as other devices such as diaphragms, flow choppers; mechanical flutters or pressure relief valves can also be used. For example, FIG. 12B illustrates the use of an underwater pressure relief system to generate broad spectrum of oscillations that are dictated by the number, calibre, orientation, and depth of the immersed tube. The flow rate, cross section of the tube orifice and the surface tension of the liquid could also impact the nature of oscillations. This oscillation mechanism differs from the bubble CPAP as the flow fluctuations occur upstream of the patient end.

Figure 13:
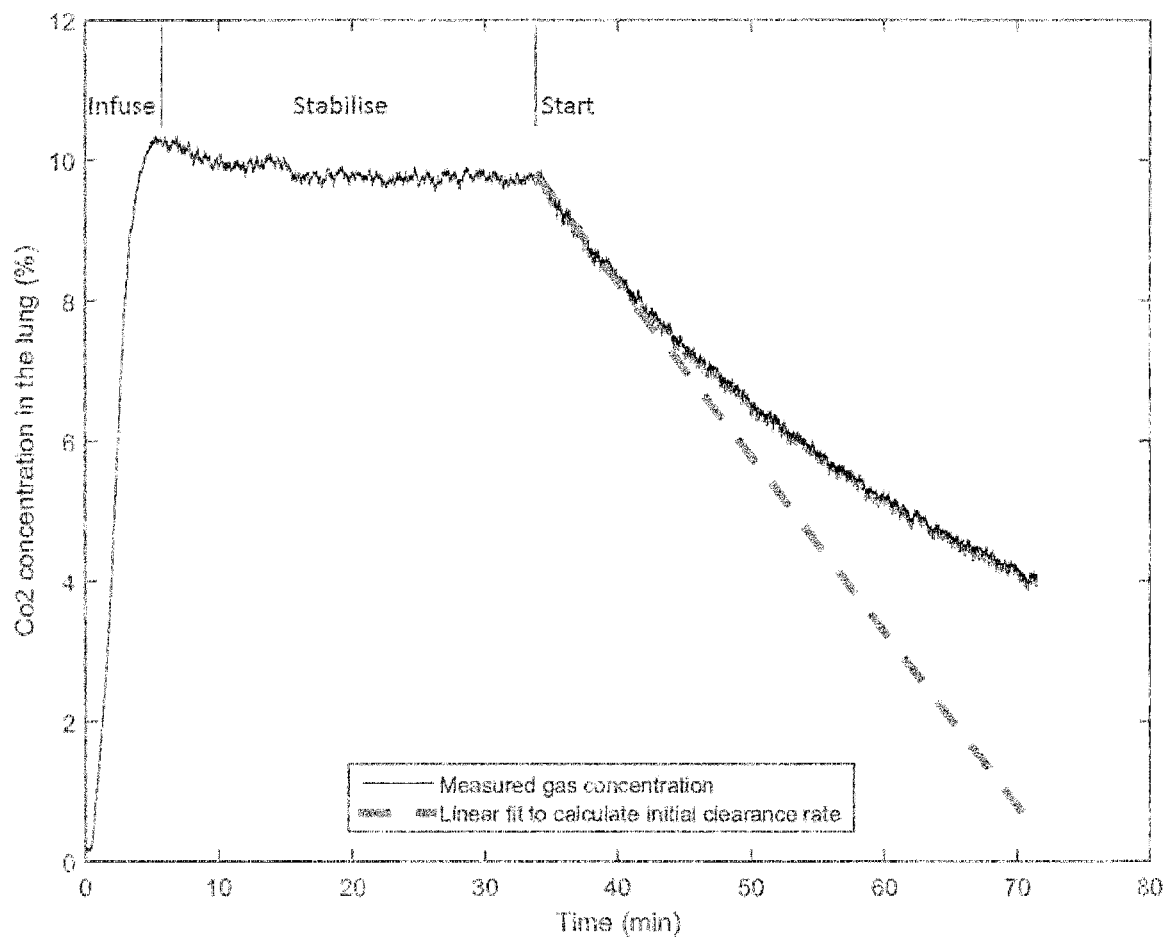
FIG. 13 shows CO2 concentration in the lung during therapy during experimental example #1.

The experimental procedure consisted of applying a fixed concentration of CO2 into the lungs (at about 9.5-10%), allowing the system to stabilise, then applying the high gas flow therapy (nasal high flow therapy—NHF) and monitoring the decay of CO2 with time from the lungs reservoir. A sample of the results is shown in FIG. 13 and includes the CO2 infusion, stabilisation period and the decay of CO2 concentration in the lung after commencement of therapy. The gradient of the dotted line signifies the decay rate.

Aside from its clinical relevance, the CO2 decay rate was used in the examples below because it is a direct measure of gas exchange between the lungs and the outside environment. In these experiments, dry air was used as the incoming high flow gas mixture but it should be noted that other gases or gaseous mixtures (such as pure oxygen saturated with water vapour at 37 degrees, mixtures of O2, N2, and helium) are also possible. The initial clearance rate was calculated as the gradient of the concentration-time curve for the first five minutes of therapy and multiplied by the lung volume to obtain gas exchange data in millilitres per minute. The data in the following examples have been normalised to that without oscillations to calculate the enhancement factor.

In one example, a vibrating mesh nebuliser was connected to the upper airway model, about 5 cm above the carina and produced a mist of water (mean particle size<4 um) to allow for flow visualisation. The gas motion was simultaneously captured with a high speed camera at 900 fps and later analysed using image processing software (ImageJ, and Matlab) to estimate time of flight and bulk gas velocity.

The following examples illustrate how varying the flow rate promotes gas exchange in the lungs, the presence of a useful frequency range where CO2 clearance is enhanced, the advantages of syncing the NHF waveform with the heart signal, the advantages of combining multiple frequencies, and the advantages of varying the wave shape. Note, the examples should not be considered exhaustive of the nature of the oscillating gas flows that will be effective and clearing CO2. Rather, they demonstrate non-limiting particular examples of the benefits of oscillating gas flows. Gas flow oscillations with parameters and parameter values (e.g. frequency, phase, amplitude and the like) other than those tested will also be effective at clearing CO2.

2.5.2 Example #1

Figure 14:
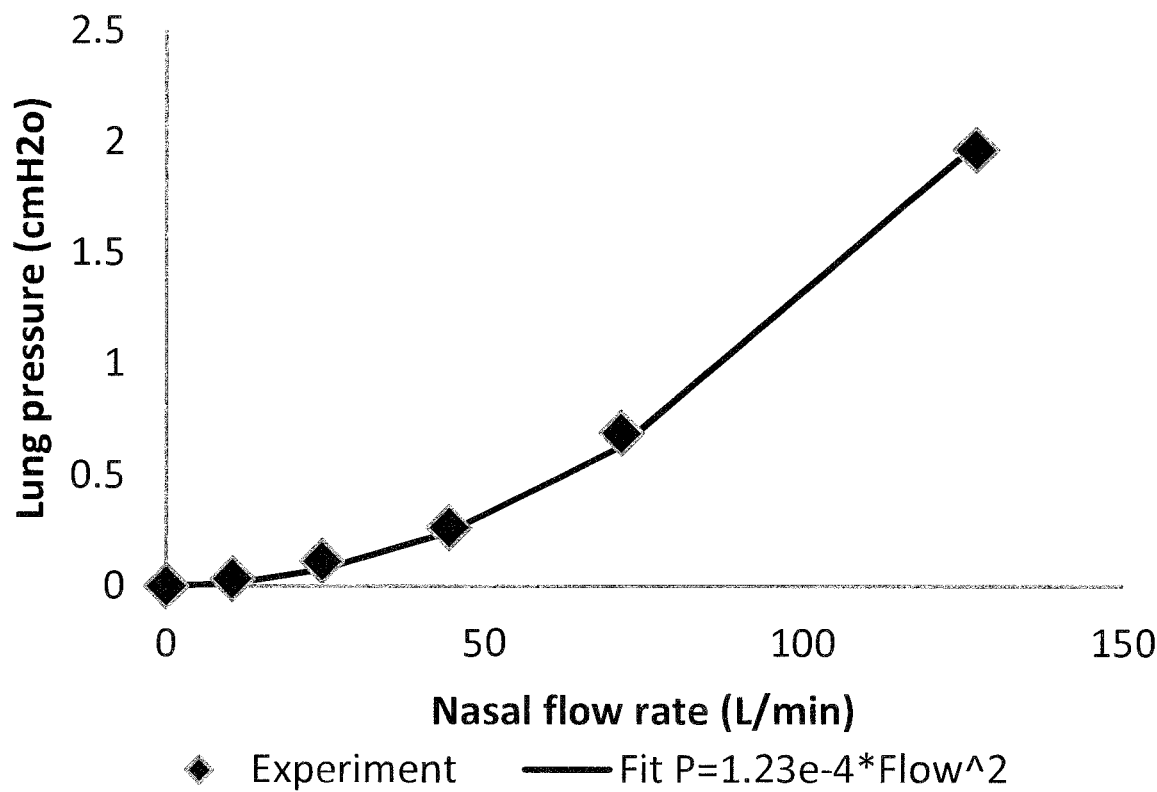
FIGS. 14 and 15A show lung pressure and flow rate during experimental example #1.
Figure 15A:
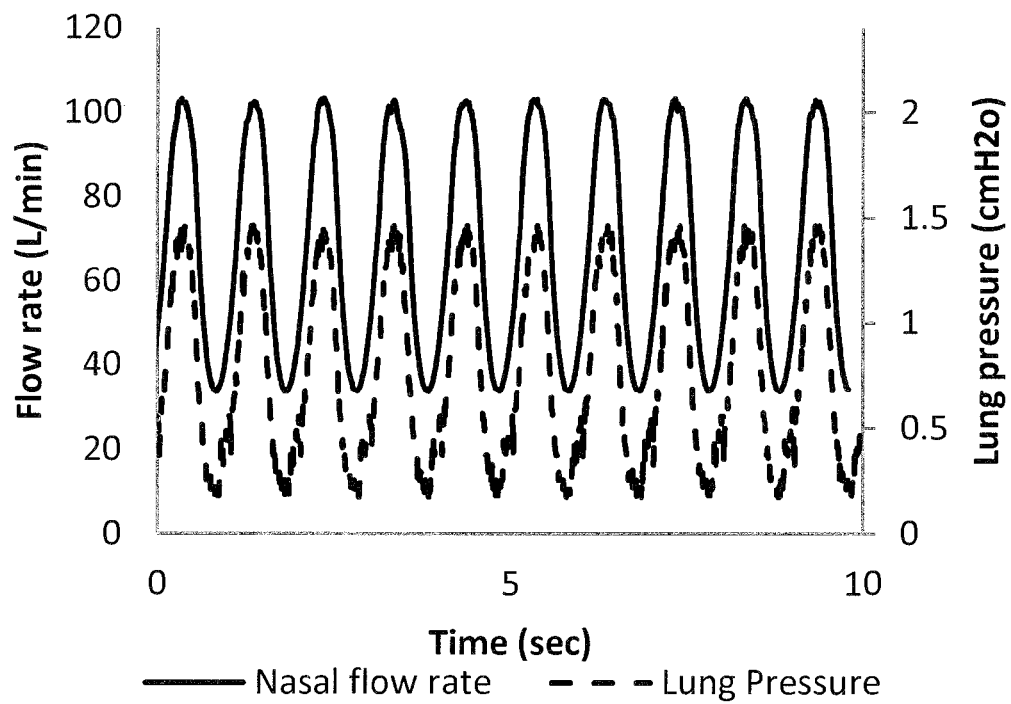

It has been previously suggested that one of the benefits of NHF, in addition to flushing parts of physiologic dead space (nasal cavity down to larynx region), is the modest increase of static lung pressure. This pressure typically scales as the approximate square of flow rate, and is on the order of 1 cmH2O (compared with ~15 cmH2O during mechanical ventilation). Pressures generated with NHF are thought to be beneficial in preventing lung atelectasis in apnoea which, in turn, improves the ventilation/perfusion matching of the respiratory system and prevents desaturation. It was surprising to find that the pressure changes generated as a result of oscillating the flow in an open HNF system were sufficient enough to promote gas movement in the upper airways and into the lungs. Examples of lung pressures as a function of constant and varying NHF rates are shown in FIGS. 14 and 15A. The FIG. 14 highlights the square nature of the pressure-flow relation and suggest that oscillating high flow is more effective than oscillating low flows (for adults, those are typically at or below 15 L/min). The high flow rates used clinically on adults could reach up to 150 L/min, or more, for example. FIG. 15A demonstrates that sinusoidal flow oscillations between 35-105 L/min at a frequency of 1 Hz can effectively promote pressure changes (with phase lag dependent on airway resistance) which in turn can improve volumetric flow into/out of the lungs as consequence of lung compliance (the pressure/volume relation).

Figure 15B:
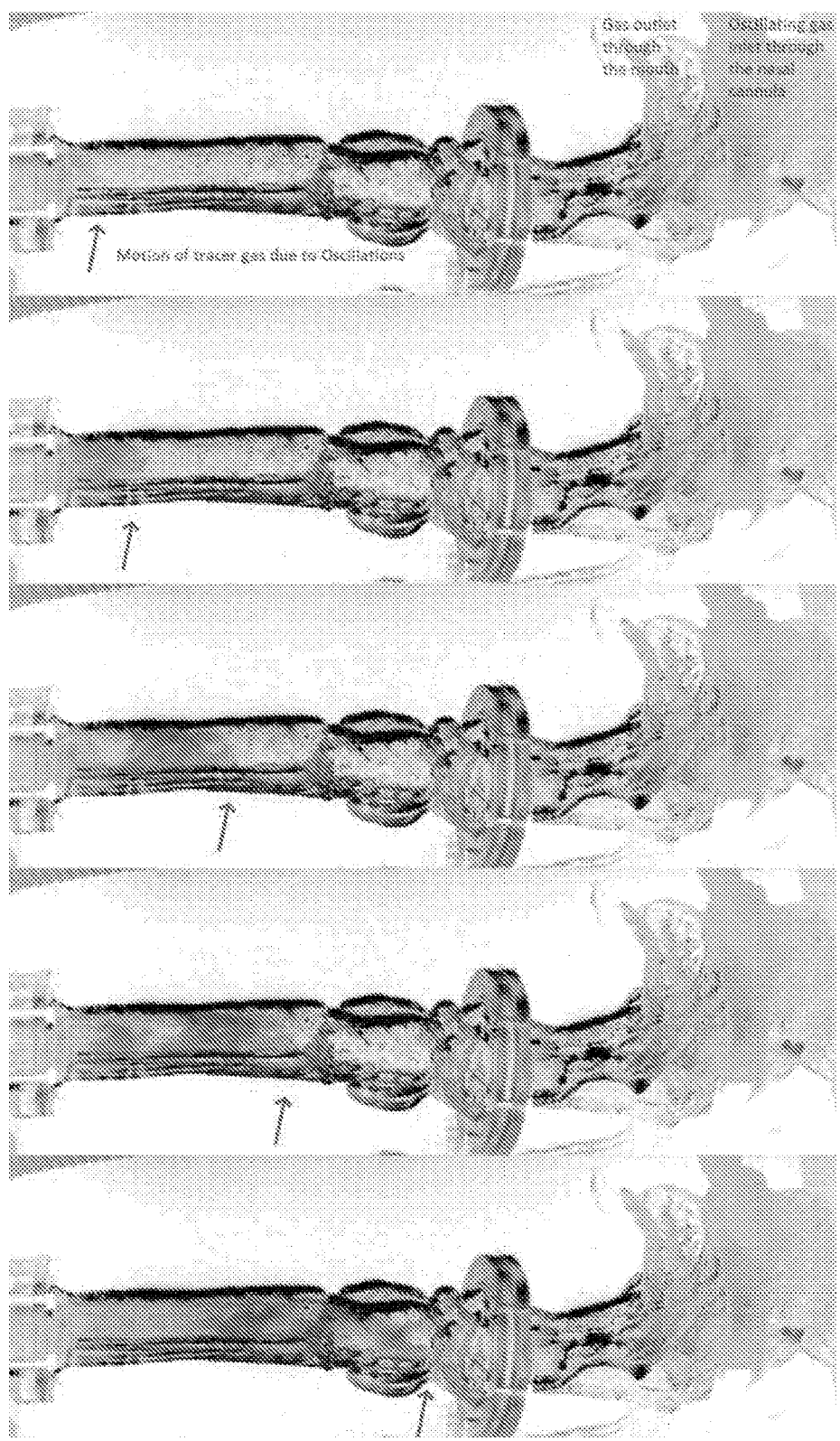
FIG. 15B shows gas flow in the airway during due to delivery of oscillating gas flow.

FIG. 15B shows a sequence of high speed images captures at about 6 ms intervals and demonstrate the motion of gas during the initial part of a sinusoidal flow oscillation between 30-100 L/min at 1 Hz. This bulk convection is fast (about 1 m/s) and is responsible for exchanging CO2 from the lower airways of the lungs with the fresh incoming gas above the larynx during each oscillation. The distance a parcel of gas travels during a single flow oscillation is not only dependant on the flow rate but also on the frequency of oscillation and the shape of the waveform as those will dictate gas acceleration, time of flight and any intra- or inter-parcel mixing that may take place. The latter is thought to be beneficial in improving gas exchange as the concentration gradients along the lung airways are reduced.

2.5.3 Example #2

Nasal high flow was delivered with nasal cannula (large) and oscillated between 30 and 100 L/min at frequencies between 0-20 Hz using a sinusoidal waveform. Cardiogenic oscillations were applied at a frequency of 1 Hz at 270 degrees out of phase to the flow with a stroke volume 22.5 mL.

Furthermore, matching the phase (i.e. synchronising) of nasal high flow and cardiogenic oscillations can provide an additional improvement in CO2 clearance by nearly a factor of 6. This suggests that it would be beneficial to have at least one waveform with a period matching that of the heart activity and with constant relative phase to that signal. Resting heart rates are typically between 40-100 bpm (0.67-1.67 Hz) but could be in the range of 30-180 bpm (0.5-3 Hz) under extreme physiology (e.g. under medical procedures or intense exercise).

It is worth noting that matching the NHF phase shift to that of cardiogenic oscillations is most meaningful when the two frequencies are identical, otherwise phase shift is inevitable.

2.5.4 Example #3

Figure 16:
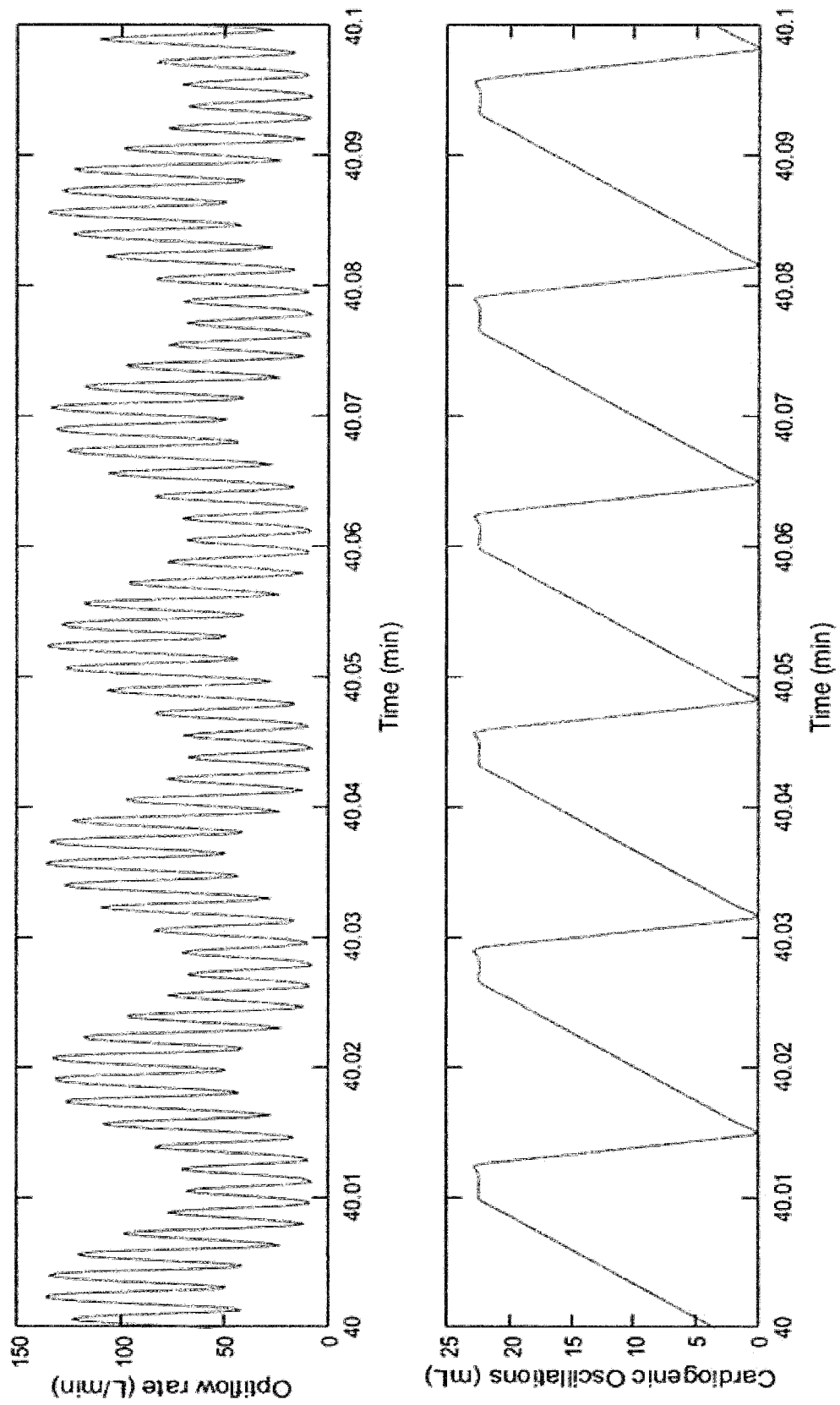
FIG. 16 shows the oscillating flow rate in relation to cardiogenic oscillations.

Nasal high flow was delivered with nasal cannula (large) and oscillated between 6 L/min (amplitude minimum) and 136 L/min (amplitude maximum) at 1 Hz and 10 Hz simultaneously (FIG. 9—top panel). The cardiogenic oscillations were applied at a frequency of 1 Hz and phase shifted between 0 and 270 degrees in 90 degree increments to the nasal high flow (see FIG. 16—bottom panel). The stroke volume was set to 22.5 mL with a frequency of 1 Hz.

Figure 17:
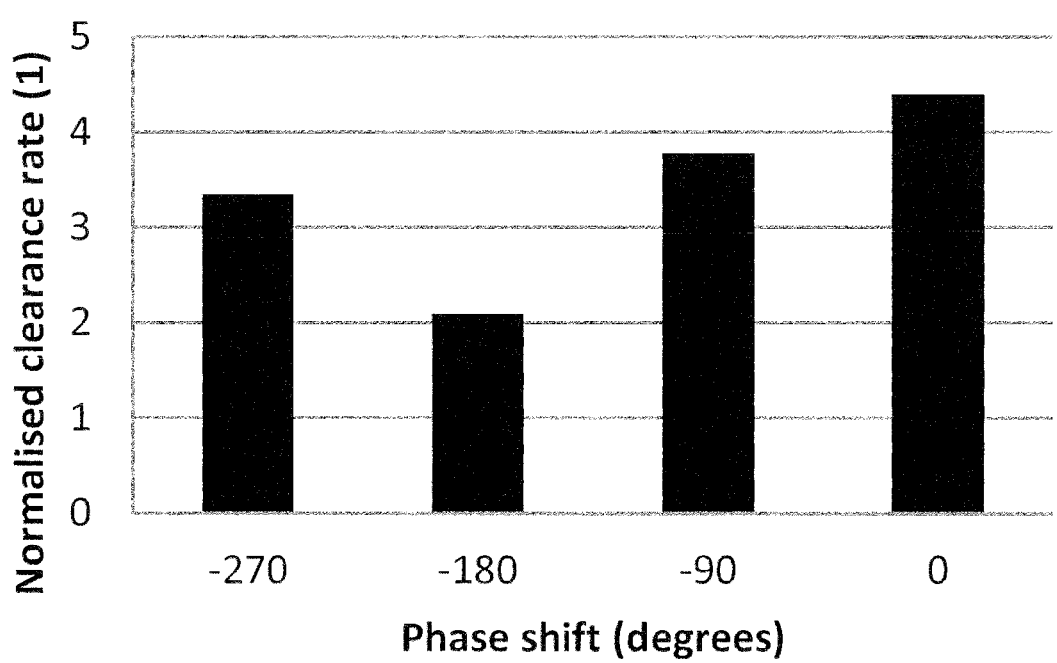
FIG. 17 shows CO2 clearance in relation to oscillatory component phase shifts.

The clearance rates indicate that syncing with the heart (a phase shift of 0) provides twice the enhancement to the contrary (a phase shift of 180 degrees) (see FIG. 17). This is because the combined effects of flow and cardiogenic volume changes in the trachea are physically added; thus, amplifying gas motion. That said, good clearance is still achieved at other phase shifts, such as or about 90 degrees, 180 degrees, 270 degrees or any other phase shift. The enhancement at any phase shift is still great than the base flow, which demonstrates that frequency matching is beneficial at any phase off-set. It is worth noting that the exact value of the phase shift is highly dependent on the shape and in some cases amplitude of the cardiogenic waveform as the addition of sinusoid and non-idealised trapezoid could be non-intuitive. In addition, the plug of gas displaced in the trachea with each cardiogenic oscillation may not take place instantaneously after every heart beat due to delays in the transmission of the pulsatile wave from the blood, through the airway tissues and into the gas where acceleration of the gas parcels would then take place. These delays in transmission would depend on the patient's physiology (e.g. heart rate, blood pressure, airway resistance etc.) and it is therefore more useful to sync with the cardiogenic pulse in the gas phase. This can be done by matching the frequency with the heart activity and either measuring, or inferring the phase shift (by calculation or CO2 clearance measurements).

Note that in a clinical setting the patient's physiology may vary with time and therefore the phase shift should also be a variable. This means that syncing with the heart signal could be in-phase (or with constant relative phase), out of phase or anything in between. In the cases where the variability is too large it might be beneficial to use a measured or calculated mean phase shift value where the NHF and heart signals are matched in a time-averaged or population-averaged sense.

Figure 2:
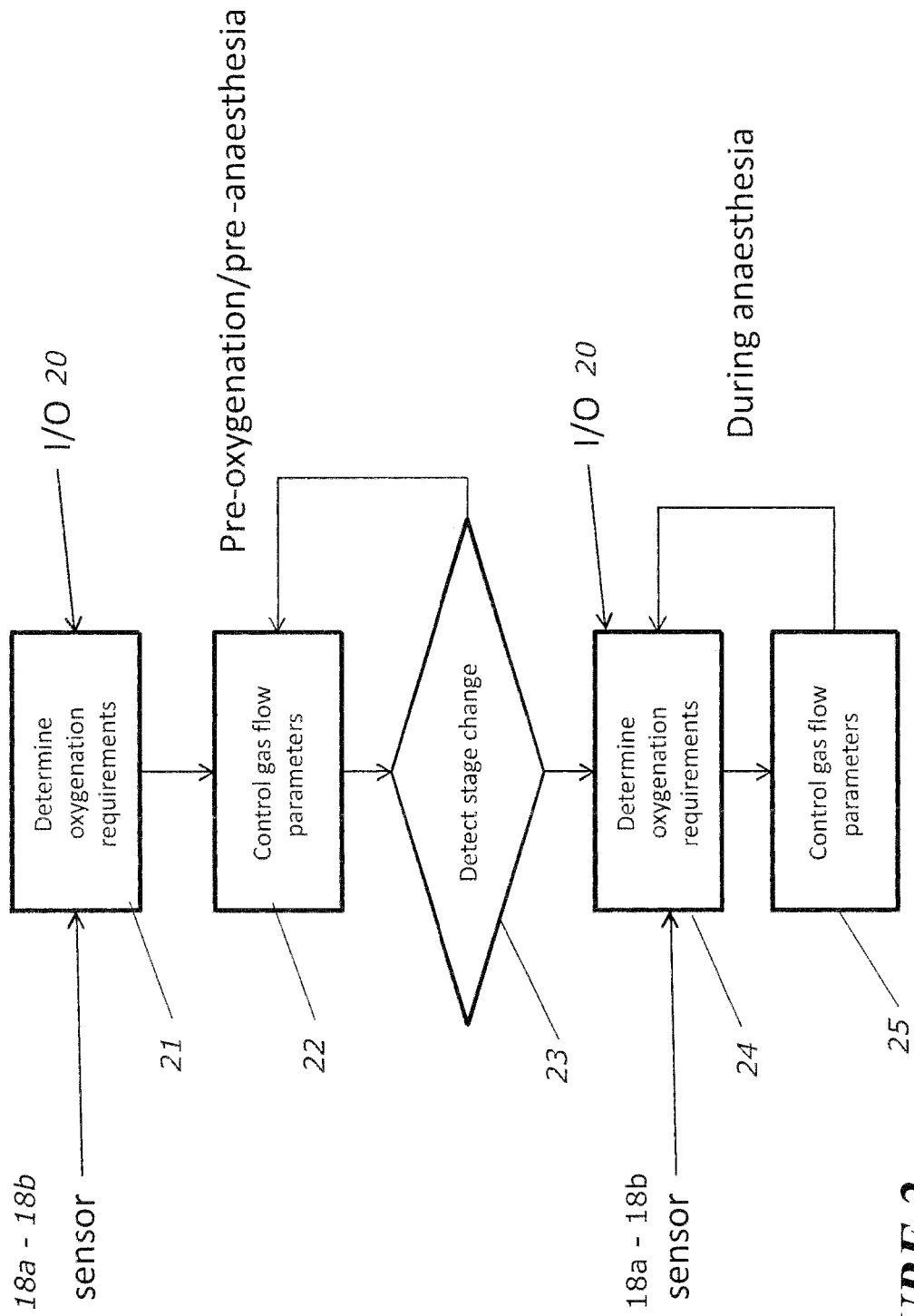
FIG. 2 illustrates a method for oxygenating a patient with high flow gas in relation to anaesthesia.

3. Embodiment of Apparatus/Method for Assisting with Oxygenation 3.1 Oxygenation During Medical Procedure Using the apparatus described above, another embodiment is provided for achieving oxygenation, during anaesthesia or other medical procedure Referring to the flow diagram in FIG. 2, the method using the system of FIG. 1 will be described. The controller is configured to carry out the determination of oxygen requirements and to control the parameters of high gas flow for oxygenation and/or CO2 removal. First, during a pre-anaesthesia stage, the controller determines oxygenation requirements of the patient, step 21. These can be oxygenation requirements that are based on the prediction of what might be required before and/or during anaesthesia based on historical/empirical data. The controller 19 receives input from the sensors 18a-18d and/or the user via the input interface 20. From that input and/or stored data (such as look up tables, historical data, parameters, relationships, the graphs or the like) the controller determines the oxygenation requirement, step 21. The determination could take place through any processing, look up table, relationship (empirical or mathematical) or the like. Non-exhaustive examples of such input and determination processing are as follows. One or more alone or in combination could be used to make the oxygen requirement determination.

The user (such as anaesthetist or other clinician, or the patient) provides, input via the interface 20, a pre-operative assessment to estimate the level of risk for every patient. This level of risk relates to the risk of the patient entering hypoxia during anaesthesia. The controller then determines oxygenation requirements, step 21, based on the level of risk and/or the user (e.g. anaesthetist or clinician) provides input indicative of the actual oxygenation requirement and/or dose/therapy settings and/or the actual parameter settings for the high flow gas delivery. Any of the input could be provided as a setting or range of settings or as one or more input values. The system could alert the user of the recommended settings or control the system to provide the settings, as to be described later.

Alternatively or additionally, and more generally, the user enters information from which oxygenation requirements can be determined, such information not necessarily directly indicating risk levels, or not being indicative of risk levels at all.

Sensor input could be used alternatively or additionally.

Next, once oxygenation requirements are determined, the controller 19 operates the flow source 12, humidifier 17 and/or other aspects of the system 10 to control the parameters of the high flow gas 13 delivered to the patient, step 22, so that the gas flow 13 meets the oxygenation requirements during a pre-anaesthesia (pre-oxygenation) stage. This can comprise altering one or more of:

flow rate of gas (such as flow rate of oxygen)
volume of gas delivered
pressure of gas
composition and/or concentration of gas Examples of user input for determining oxygenation requirements and the resultant parameter settings are as follows.

The user enters the value on a scale. For example the user could choose a number from 1 (minimal risk) to 10 (high risk). The system could then choose the optimal settings for that scale number.

The user enters information such as age, weight, BMI, lung volumes, metabolic rate, body fat measure (e.g. percentage) and/or other patient factors that could be used individually or any combination to choose the optimal therapy settings (oxygen requirements). For example, a sum score method could be used with two or more of the factors listed. This can be used to predict the level of support (oxygenation) that will be required The user enters pre-existing patient conditions. For example, if a patient is at risk of barotrauma the flow could be minimised to meet peak inspiratory demand but not deliver excess flow.

Existing limits on hardware could be used to choose the optimal therapy settings. For example, if the surgical environment is experiencing a shortage in oxygen the settings could be altered. 100% oxygen could be delivered only during inspiration and the flow could be set to meet the patient's peak inspiratory demand to ensure minimal wastage Different levels of support could be optimal in different stages of undergoing anaesthesia. The high flow system 10 can optionally detect when a change in stage has occurred and alert the user or automatically determine new oxygenation requirements and/or change the gas flow parameters to me those new requirements. For example, after the pre-oxygenation stage, the patient is administered the anaesthesia and enters and anaesthesia stage. Breathing function can diminish and the patient can become apnoeic. Different oxygenation requirements exist to those pre-anaesthesia.

Therefore, the controller 19 is further configured to detect the anaesthesia stage (or change in anaesthesia stage), step 23. Possible methods for detecting a change in state are as follows.

The controller uses the pressure waveform (from a pressure sensor) to detect when the patient is breathing or not (e.g. transition from pre-oxygenation to apnoea).

The controller uses the expired CO2 waveform (from a sensor) to detect when the patient is breathing or not (e.g. transition from pre-oxygenation to apnoea)

While the controller 19 is monitoring the state, step 32, the high flow gas 13 is delivered as per the parameters previously determined and set. After a change in stage is determined (such as transitioning from the pre-oxygenation stage to the anaesthesia stage) the controller/system 19/10 can continue delivering gas flow 13 with the same parameter settings. However, the system 10 can also go into a monitoring phase, step 24, wherein by the oxygenation requirements are re-determined, optionally in a continuously or periodic manner, step 24. Again previous or fresh input from a user via the input interface 20 can be used to determine the oxygenation requirements, in addition or alternatively to using sensor input 18a-18d. The oxygenation requirement can be determined in the same manner as described above for the pre-oxygenation stage, with the possible difference being that it is re-determined continuously or periodically based on updated input from the sensors and/or user.

The gas flow 13 parameters are then adjusted by the controller 19 to meet new oxygen requirements, these parameters being the same as described above, step 25. Even if updated input is not received, the oxygenation requirement might be re-determined on the basis that the stage of anaesthesia had changed, or alternatively the oxygenation requirement is not specifically re-determined, but a different oxygenation requirement is presumed and the high flow gas parameters are set accordingly for the new stage.

3.2 Oxygenation Using Flow

Figure 3:
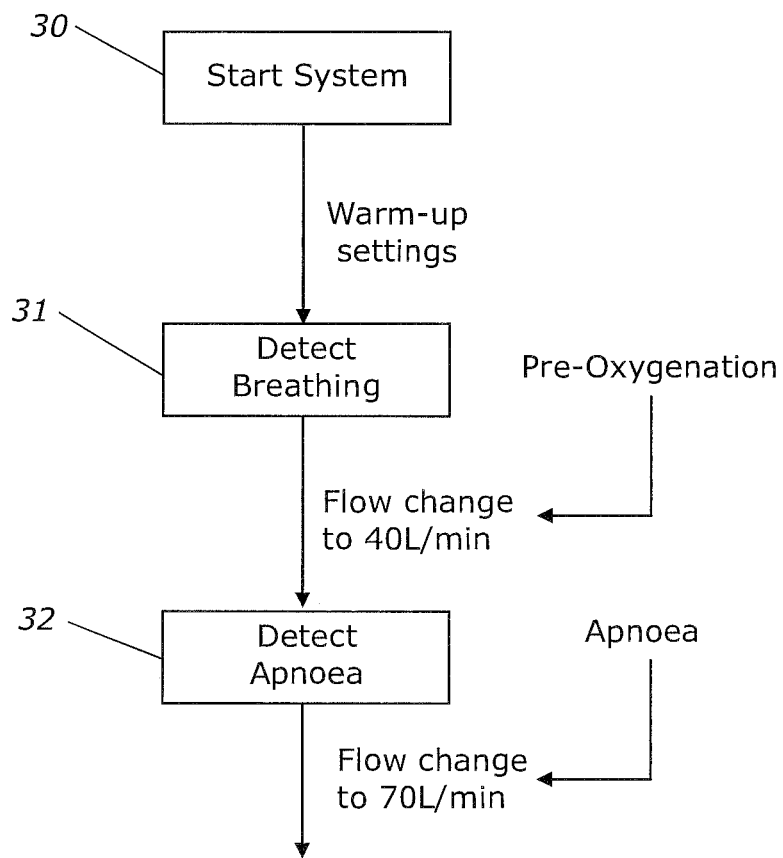
FIG. 3 illustrates a method of determining a stage of anaesthesia.

A particular non-limiting example of the function due to change in anaesthesia state as shown in FIG. 3. After the system started, step 30, the system monitors the patient and detects breathing, step 31, and determines a pre-oxygenation stage. The system provides gas flow parameters, including a flow rate of 40 L per minute, which are suitable for the pre-oxygenation stage, based on typical oxygenation requirements. After further monitoring of the patient, the system detects an apnoea, and assumes that the anaesthesia stage has started, step 32. That changes the parameters of the gas flow to a flow rate of 70 L per minute which meets the oxygenation requirements of the apnoeic stage, step 32.

A continuous supply of oxygen and removal of carbon dioxide is important to sustain healthy respiratory function. In addition to the method described above relating to determining and providing oxygenation requirements, the system can also be configured to monitor supply of oxygen and removal of carbon dioxide, step 24 as in FIG. 2. Possible non-limiting methods of monitoring these comprise:

monitoring expired O2 and CO2 (using e.g. sensors)
monitoring transcutaneous O2 and CO2
monitoring blood gases (e.g. pulse oximeter)
monitoring SpO2
monitoring partial pressure of O2 and/or CO2
monitoring RIP
  any other suitable physiological parameters described herein.

In step 24, the trends/values of these parameters described above could be used to detect when the therapy settings (gas flow parameters) could be changed. The system is configured to then alert the user or automatically control the therapy dose (that is, gas parameters).

For example, if the SpO2 starts to decrease past 90%, the flow and or oxygen concentration (if not already at 100%) could increase to provide a higher level of support, step 25. If the end-tidal CO2 value or trend shows an increase, the therapy support could increase as a higher level of support is needed, step 25. This should not be limited to oxygen and carbon dioxide. Other measured parameters (e.g. heart rate, blood pressure) could also be used to change the therapy dose settings.

In further embodiments, when the predicted or monitored pre-oxygenation or apnoeic time is small, the gas parameters can be changed accordingly. For example, if the estimated time of the anaesthesia stages (pre-oxygenation or during anaesthesia/apnea) is too short, the gas parameters can be adjusted to provide a higher level of support for more time—for example the oxygen concentration, flow rate, oxygen volume, pressure and/or gas composition can be changed, for example.

As relatively high gas delivery flow rates may be used with the embodiments or configurations described herein, the gases being supplied or delivered to the user or patient can may be delivered to different parts of the user's or a patient's airway.

For example, according to those various embodiments and configurations described herein, a flow rate of gases supplied or provided to an interface or via a system, such as through a flow path, may comprise, but is not limited to, flows of 15 litres/min to 150 litres/min and optionally at least about 40, 50, 60, 70, or 80 L/min, or more, and useful ranges may be selected between any of these values (for example, about 40 to about 80, about 50 to about 80, about 60 to about 80, about 70 to about 80 L/min, or any other subrange of 15 litres/min to 120 Litres/min).

Such relatively high flow rates of gases may assist in providing the supplied gases into a user's airway, or to different parts of a user's airway, for example such flow rates may allow for a delivery of such gases to the upper or lower airway regions as shown in FIG. 4. Upper airway region typically includes the nasal cavity, pharynx and larynx, while the lower airway region typically includes the trachea, primary bronchi and lungs.

The embodiments described can utilise the knowledge of the respiratory flow wave and/or the transition between inspiration and expiration. For example methods and apparatus for respiratory flow wave, meeting (e.g. peak) inspiratory demand and estimating (e.g. peak) inspiratory demand could be used. It should also be noted that the following can utilise switching modes of operation between inspiration and expiration. The exact moment of switching should not be limited to the exact transition point.

As described above, gas flow parameters are changed to provide the required oxygenation and/or removal of CO2. This can be by way of adjusting e.g. gas flow rate and/or pressure.

The foregoing description of the invention includes preferred forms thereof. Modifications may be made thereto without departing from the scope of the invention.

The invention claimed is:

1. An apparatus for oxygenation or $CO_2$ clearance of a patient, or a combination thereof, during a medical procedure wherein during the medical procedure the patient is apnoeic for at least a portion of the medical procedure or the patient is under anesthesia causing diminished or risk of diminished respiratory function, comprising:
  a flow source or a connection for a flow source configured to provide a gas flow;
  a gas flow modulator; and
  a controller configured to control a flow rate of the gas flow during a preoxygenation stage of the medical procedure or when the patient is under anesthesia, the controller configured to control the flow rate by controlling the gas flow modulator to oscillate the flow rate based on an oscillating flow rate component and a base flow rate component to provide a varying gas flow with one or more frequencies, wherein the controller is configured to control the gas flow between a set flow rate before the patient is apneic, or has a diminished, or is at risk of diminished, respiratory function and a base flow rate of the base flow rate component when the patient is apneic, or has a diminished, or is at risk of diminished, respiratory function; and wherein the apparatus is configured to provide the gas flow to a non-sealing patient interface.

2. The apparatus according to claim 1 wherein the oscillating flow rate component has an oscillating flow rate and the controller is configured to control the gas flow modulator to provide the oscillating flow rate within a range of about 0 litres/min to about 375 litres/min.

3. The apparatus according to claim 2 wherein the base flow rate of the base flow rate component is within a range of about 0 litres/min to about 375 litres/min.

4. The apparatus according to claim 2 wherein the base flow rate of the base flow rate component is in a range of about 0.2 litres/min per patient kilogram to about 2.5 litres/min per patient kilogram.

5. The apparatus according to claim 2 wherein the flow source or the connection for the flow source is configured to provide the gas flow for use on persons greater than about 30 kg.

6. The apparatus according to claim 2 wherein the oscillating flow rate comprises one or more frequencies in a range of about 0.1 Hz to about 3 Hz.

7. The apparatus according to claim 2 wherein the oscillating flow rate is in a range of 0.05 litres/min per patient kilogram to 2 litres/min per patient kilogram.

8. The apparatus according to claim 2 wherein the flow source or the connection for the flow source is configured to provide the gas flow for use on persons within a range of about 0.3 to 30 kg.

9. The apparatus according to claim 2 wherein a base flow rate of the base flow rate component is about 8 litres/min for a person under about 2 kilograms.

10. The apparatus according to claim 1 wherein the gas flow modulator comprises an underwater pressure release valve, an oscillatable diaphragm, an in-line linear actuator, a flow chopper, an aerodynamic flutter valve, a mechanical flutter valve, or a proportional valve.

11. The apparatus according to claim 1 wherein the gas flow modulator is in or after the flow source.

12. The apparatus according to claim 1 wherein the gas flow has an oxygen fraction of 100%, or in a range of 30-40% or in a range of 40-50% or in a range of 60-70% or in a range of 80-90% or in a range of 90-100%.

13. The apparatus according to claim 1 wherein the gas flow is air.

14. The apparatus according to claim 1 wherein the non-sealing patient interface comprises or is configured for use with a high flow nasal cannula.

15. The apparatus according claim 1 further comprising a humidifier to humidify the gas flow before or after it is oscillated.

16. The apparatus according to claim 1 wherein the controller is configured to determine when the apnoea in the patient has commenced or to detect an anaesthesia stage or change in anaesthesia stage in the patient.

17. The apparatus according to claim 10 wherein the gas flow modulator is or comprises the proportional valve, and the proportional valve has a variable size orifice that is variable based on an electrical signal.

18. The apparatus according to claim 3 wherein the base flow rate is within a range of about 30 litres/min to about 90 litres/min.

19. The apparatus according to claim 1 wherein the one or more frequencies comprises at least two frequencies.

20. The apparatus according to claim 19 wherein the at least two frequencies are in a range of about 0.1 Hz to about 3 Hz.

21. The apparatus according to claim 1 wherein the base flow rate is higher than the set flow rate.

22. A method for oxygenation or $CO_2$ clearance of a patient, or a combination thereof, comprising:

controlling, via a controller, a gas flow to the patient via a non-sealing nasal interface during a preoxygenation stage of a medical procedure or when the patient is under anesthesia;

determining or detecting a stage of the medical procedure; and based on the stage determined or detected, varying the gas flow delivered to the patient by oscillating a flow rate of the gas flow based on an oscillating flow rate component and a base flow rate component when the patient is apneic or has a diminished risk or is at risk of diminished respiratory function;

wherein the varying gas flow comprises a set flow rate before the patient is apneic, or has a diminished, or is a risk of diminished, respiratory function and a base flow rate of the base flow rate component when the patient is apneic, or has a diminished, or is at risk of diminished, respiratory function.

23. The method according to claim 22 wherein a base flow rate of the base flow rate component is in a range of about 0.2 litres/min per patient kilogram to about 2.5 litres/min per patient kilogram.

24. The method according to claim 22 wherein the non-sealing nasal interface comprises or is configured for use with a high flow nasal cannula.

25. The method according to claim 22 wherein the determining or detecting the stage of the medical procedure further comprises determining when the apnoea in the patient has commenced or detecting an anaesthesia stage or change in anaesthesia stage in the patient.

26. The method according to claim 22 wherein the varying gas flow comprises at least two frequencies.

27. The method according to claim 26 wherein the at least two frequencies are in a range of about 0.1 Hz to about 3 Hz.

28. The method according to claim 22 wherein the base flow rate is higher than the set flow rate.

* * * * *